US012397296B2

United States Patent
Xiao

(10) Patent No.: US 12,397,296 B2
(45) Date of Patent: Aug. 26, 2025

(54) SYSTEMS AND METHODS FOR MOTILE SPERM DETERMINATION

(71) Applicant: Flow Health Services Incorporated, Toronto (CA)

(72) Inventor: Sa Xiao, Toronto (CA)

(73) Assignee: Flow Health Services Incorporated, Toronto (CA)

( * ) Notice: Subject to any disclaimer, the term of this patent is extended or adjusted under 35 U.S.C. 154(b) by 0 days.

(21) Appl. No.: 18/921,829

(22) Filed: Oct. 21, 2024

(65) Prior Publication Data

US 2025/0249457 A1    Aug. 7, 2025

Related U.S. Application Data

(60) Provisional application No. 63/550,919, filed on Feb. 7, 2024.

(51) Int. Cl.
*B01L 3/02*    (2006.01)
*B01L 3/00*    (2006.01)
(Continued)

(52) U.S. Cl.
CPC .... *B01L 3/502761* (2013.01); *G01N 33/5091* (2013.01); *B01L 2200/027* (2013.01);
(Continued)

(58) Field of Classification Search
None
See application file for complete search history.

(56) References Cited

U.S. PATENT DOCUMENTS

| | | | | |
|---|---|---|---|---|
| 3,886,047 A | * | 5/1975 | Billups, Jr. | ............ C12M 25/06 |
| | | | | 435/305.3 |
| 5,462,874 A | * | 10/1995 | Wolf | ...................... C12M 23/12 |
| | | | | 435/297.5 |

(Continued)

OTHER PUBLICATIONS

Mascarenhas MN, Flaxman SR, Boerma T, Vanderpoel S, Stevens GA., "National, regional, and global trends in infertility prevalence since 1990: a systematic analysis of 277 health survey", PLoS Med. 2012;9(12):e1001356. doi: 10.1371/journal.pmed.1001356.

(Continued)

*Primary Examiner* — Elizabeth A Robinson
*Assistant Examiner* — Brittany I Fisher
(74) *Attorney, Agent, or Firm* — Bookoff McAndrews, PLLC

(57) ABSTRACT

Systems and methods for male fertility analysis may include: loading an aliquot of a male fertility sample into a chamber of an analysis system via an inlet, the chamber having an opening covered over by a porous membrane and a concave bottom opposite the opening; introducing media so that the membrane acts as a migration path for motile sperm; removing the media and a motile portion of the aliquot from the system into a container; sealing the container; and transporting the sealed container and a remainder of the male fertility sample to a testing facility. The testing facility may: determine a first concentration of the portion of the sample from the first container; determine a second concentration of the remainder; and estimate a percentage of total motile sperm for the sample based on the first concentration, the second concentration, and a predetermined relationship between portions and remainders of samples.

20 Claims, 17 Drawing Sheets

(51) Int. Cl.
  *G01N 33/50* (2006.01)
  *G01N 35/10* (2006.01)
  *C12N 5/076* (2010.01)

(52) U.S. Cl.
  CPC ............ *B01L 2200/0652* (2013.01); *B01L 2200/0689* (2013.01); *B01L 2200/12* (2013.01); *B01L 2200/18* (2013.01); *B01L 2300/021* (2013.01); *B01L 2300/042* (2013.01); *B01L 2300/0681* (2013.01); *C12N 5/061* (2013.01)

(56) References Cited

U.S. PATENT DOCUMENTS

| | | | | |
|---|---|---|---|---|
| 6,576,458 | B1 * | 6/2003 | Sarem | C12M 29/14 435/297.5 |
| 6,593,136 | B1 * | 7/2003 | Geiss | C12M 23/44 435/363 |
| 10,422,737 | B2 | 9/2019 | Demirci et al. | |
| 2008/0299649 | A1 * | 12/2008 | Martin | C12M 23/38 435/297.1 |
| 2013/0017129 | A1 * | 1/2013 | Shioyama | B01L 3/502 422/513 |

OTHER PUBLICATIONS

Inhorn MC, Patrizio P., "Infertility around the globe: new thinking on gender, reproductive technologies and global movements in the 21st century", Hum Reprod Update. 21, 411-426 (2015). doi: 10.1093/humupd/dmv016.

Schmidt, L., "Social and psychological consequences of infertility and assisted reproduction—what are the research priorities?", Human Fertility, 12(1), 14-20 (2009).

Huang, J. Y. J. & Rosenwaks, Z. in Human Fertility: Methods and Protocols (eds Zev Rosenwaks & Paul M. Wassarman) 171-231 (Springer New York, 2014).

Agarwal, A., Mulgund, A., Hamada, A. & Chyatte, M. R., "A unique view on male infertility around the globe", Reproductive Biology Endocrinology (2015) 13:37. DOI 10.1186/s12958-015-0032-1.

Virtanen, H. E., Jørgensen, N. & Toppari, J., Abstract Only for "Semen quality in the 21st century", Nature Reviews Urology, vol. 14, pp. 120-130 (2017).

Kumar, N. & Singh, A. K., "Trends of male factor infertility, an important cause of infertility: A review of literature", J. Hum. Reprod. Sci. 2015;8:191-6. DOI 10.4103/0974-1208.170370.

Matsuura, K. et al., "Paper-based diagnostic devices for evaluating the quality of human sperm", Microfluid Nanofluid (2014) 16:857-867. DOI 10.1007/s10404-014-1378-y.

Nosrati, R. et al., :Paper-Based Quantification of Male Fertility Potential, Clinical Chemistry 62, 458-465 (2016). DOI 10.1373/clinchem.2015.250282.

Coppola, M. A. et al., "SpermCheck® Fertility, an immunodiagnostic home test that detects normozoospermia and severe oligozoospermia", Human Reproduction, vol. 25, No. 4, pp. 853-861, 2010. DOI 10.1093/humrep/dep413.

* cited by examiner

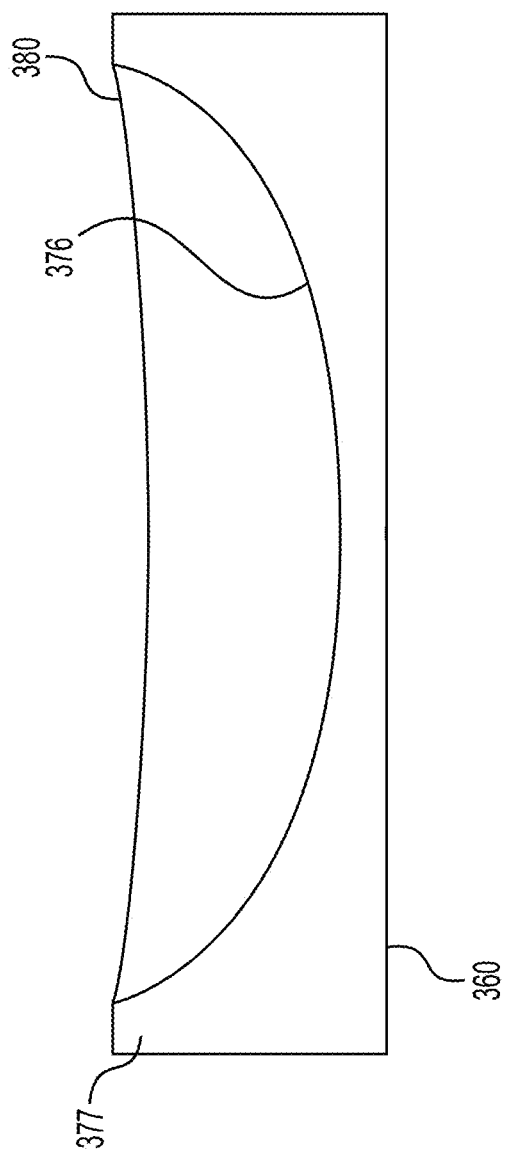

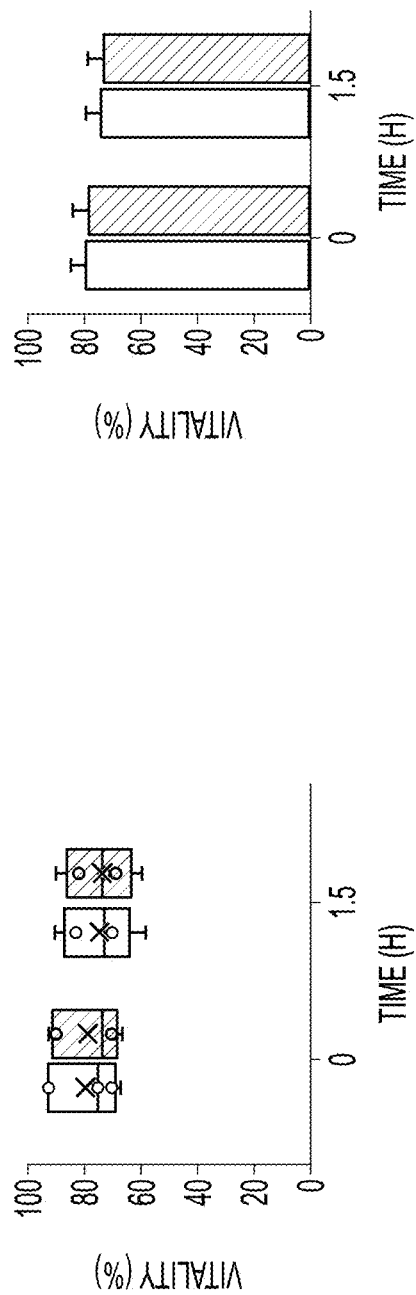
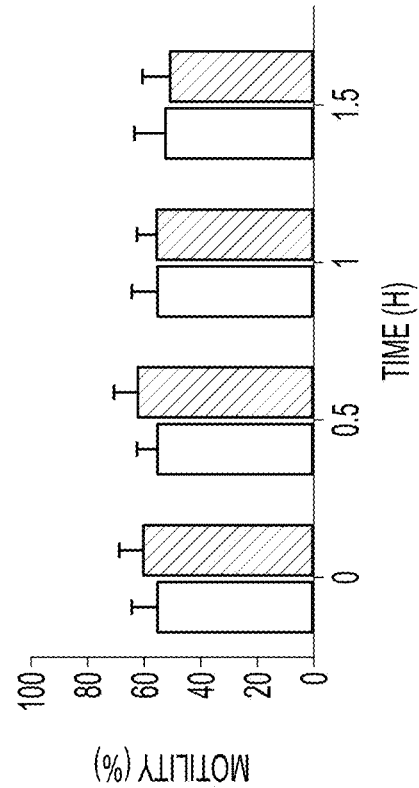
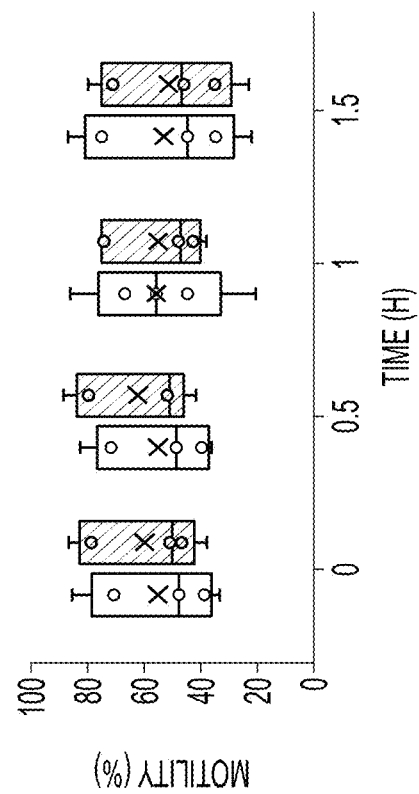

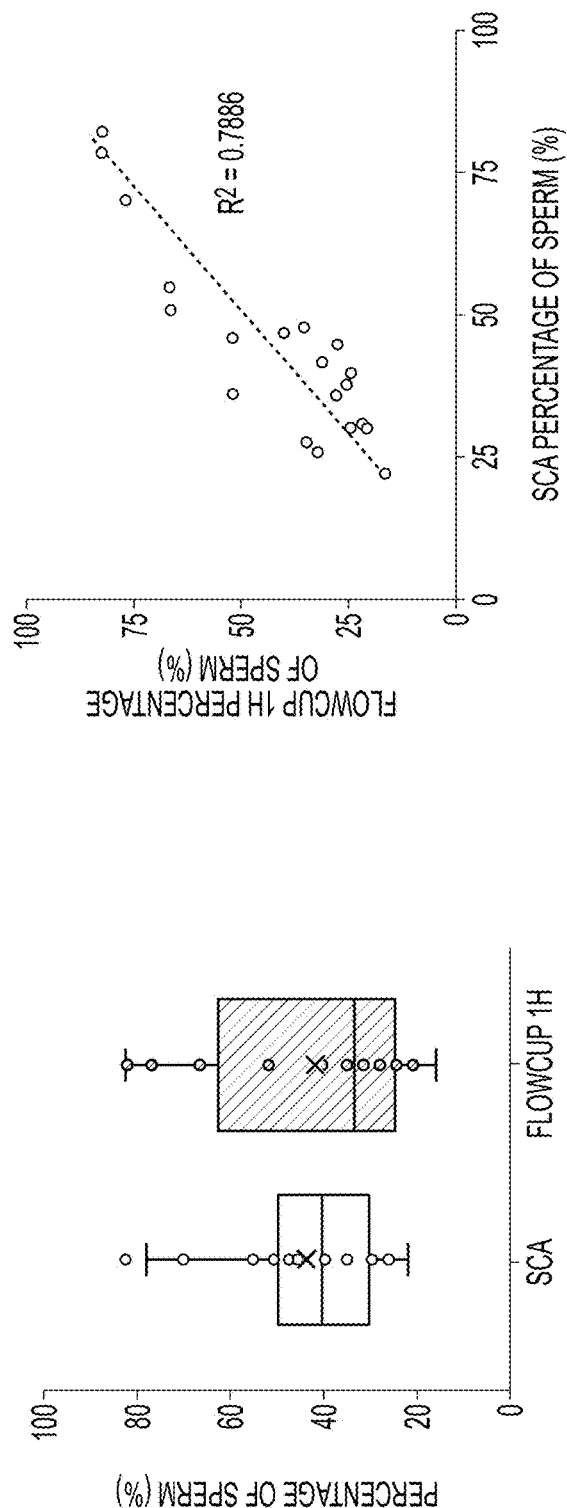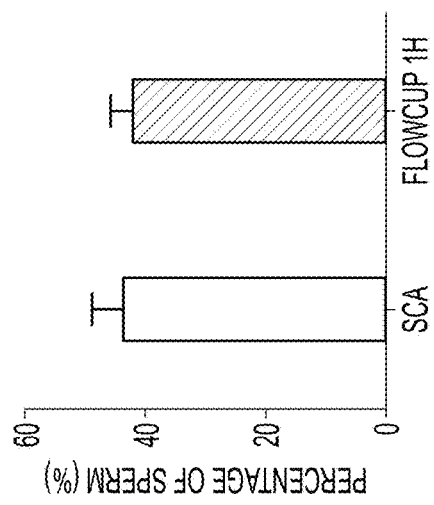
FIG. 13C
FIG. 13D
FIG. 13B

SYSTEMS AND METHODS FOR MOTILE SPERM DETERMINATION

RELATED APPLICATIONS

This application is a non-provisional application of, and claims the benefit of priority to, U.S. Provisional Application No. 63/550,919, filed on Feb. 7, 2024, the entirety of which is incorporated herein by reference.

TECHNICAL FIELD

Various embodiments of the present disclosure relate generally to systems and methods for male fertility testing, and more particularly to systems and methods for remote pre-processing of a male fertility sample for later quantitative analysis.

BACKGROUND

Male infertility is a major global concern, and is characterized by an ejaculate of reduced fertilization capacity (e.g., insufficient sperm counts or low-quality sperm with regard to one or more factors such as sperm motility, morphology, or DNA integrity). Semen analysis, or sperm diagnostics, is vital in assessing the fertile state of the male and involves evaluation of the sperm count, morphology, motility, and vitality. The assessment of sperm motility, in particular, is important in dictating the overall quality of the sample, and generally must be performed within one hour of ejaculation to ensure no losses in sperm motility for an accurate evaluation of the motility percentage.

Mircofluidics devices have been developed to perform at-home qualitative assessments of various factors, e.g., the female pregnancy test, the COVID-19 rapid antigen test, and others. In the context of male fertility, devices have been developed that provide a qualitative assessment of total sperm count, motility, etc. However, such qualitative analysis solutions generally lack accuracy and/or reliability. Such devices generally only operate on a small portion of a sample, with the result that quantitative information in the rest of the sample is lost. In many cases the results of such testing solutions are non-quantifiable, non-diagnostic, or subjective or difficult to read. For example, microfluidics testing results may be expressed as a coloration, color intensity, or the like, e.g., the appearance of a colored test-strip if sperm concentration is above a predetermined threshold. Other solutions have been developed, e.g., the use of a smartphone camera or the like to analyze a small portion of a sample on a slide. However, such solutions generally suffer from similar challenges as those mentioned above.

Thus, conventionally, quantitative semen analysis is performed in a laboratory setting, e.g., with patients either physically at a laboratory setting or dropping off a sample collected remotely but within a narrow one-hour time window (e.g., dropping the sample off at the laboratory within 60 minutes of collection). However, these methods are challenged by the requirements of lab accessibility and patient availability, as well as sample transfer processes that can reduce sperm motility and quality. For example, even with the aid of buffers to help maintain the viability of sperm during transport to a lab, many factors result in such solutions having insufficient or suboptimal results, e.g., ineffectiveness of the buffer, temperature fluctuations during transport, unexpected lengthy transport durations, etc.

The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

In at least one aspect of the present disclosure, an exemplary system for male fertility analysis may include: a first portion, including: a chamber with an opening and a concave bottom opposite the opening; and an inlet into the chamber; a second portion; and a porous membrane extending over the opening of the chamber and secured between the first portion and the second portion, such that the porous membrane is configured to act as a migration path for a motile portion of an aliquot of a male fertility sample loaded into the chamber via the inlet to move into media loaded into the second portion, wherein the second portion is operable to pour the media and the motile portion of the aliquot of the male fertility sample out from the system.

In at least one further aspect of the present disclosure, an exemplary method for male fertility analysis may include: receiving a first container including a portion of an aliquot of a male fertility sample, the portion having been extracted from the aliquot based on motility; receiving a second container including a remainder of the male fertility sample; determining a first concentration of the portion of the male fertility sample from the first container; determining a second concentration of the remainder of the male fertility sample from the second container; and generating an estimate of a percentage of total motile sperm for the male fertility sample based on the first concentration, the second concentration, and a predetermined relationship between portions and remainders of male fertility samples.

In at least one additional aspect of the present disclosure, an exemplary method for male fertility analysis may include: at a location remote from a testing facility: obtaining an aliquot of a male fertility sample; loading the aliquot into a chamber in a first portion of a male fertility analysis system via an inlet in the first portion, the chamber having a concave bottom and an opening opposite the concave bottom that is covered over by a porous membrane positioned between the first portion and a second portion; sealing the inlet via a first cap; introducing media into an opening of the second portion that is in communication with the porous membrane, such that the porous membrane acts as a migration path for a motile portion of the aliquot to move into the media in the second portion; operating the male fertility analysis system to pour the introduced media out into a container, the media poured out into the container including the motile portion of the aliquot; sealing the container via a second cap; and transporting the sealed container and a remainder of the male fertility sample to the testing facility.

In another aspect, a system for male fertility analysis may include a basket and a container with an opening configured to removably receive the basket. The basket may include a base portion having: a chamber with an opening; and an inlet into the chamber; a support structure; and a porous membrane extending over the opening of the chamber. The container may be configured such that at least the base portion and the porous membrane are submergible by media within the container. In an embodiment, the chamber may include a concave bottom. In an embodiment, the support structure may extend over the porous membrane.

In a further aspect, a method for male fertility analysis may include: at a location remote from a testing facility: obtaining an aliquot of a male fertility sample; loading the aliquot into a chamber in a base portion of a basket via an inlet in the base portion, the chamber having an opening covered over by a porous membrane positioned between the base portion and a support structure; submerging at least the base portion of the basket and the porous membrane into media disposed in a container for a predetermined period of time, such that an interface is formed between the aliquot, the porous membrane, and the media; removing the basket from the container; sealing the container via a cap; and transporting the sealed container and a remainder of the male fertility sample to the testing facility.

In another aspect of the present disclosure, a method for male fertility analysis may include: receiving, from a remote location, a first container including a portion of an aliquot of a male fertility sample, the portion having been extracted from the aliquot based on motility; receiving a second container including a remainder of the male fertility sample; determining a first concentration of the portion of the male fertility sample from the first container; determining a second concentration of the remainder of the male fertility sample from the second container; and generating an estimate of a percentage of total motile sperm for the male fertility sample based on the first concentration, the second concentration, and a predetermined relationship between portions and remainders of male fertility samples.

In another aspect, a kit for collecting a male fertility sample may include: a basket, a first container with an opening configured to removably receive the basket, media for the first container, a second container configured to receive a male fertility sample, and a loading device. The basket may include: a base portion having: a chamber with an opening; and an inlet into the chamber; a support structure; and a porous membrane extending over the opening of the chamber and positioned between the base portion and the support structure. The loading device may be operable to load an aliquot of the male fertility sample into the chamber via the inlet. The first container may be configured such that at least the base portion and the porous membrane are submergible by media within the first container. The second container may be configured to receive a male fertility sample.

It is to be understood that both the foregoing general description and the following detailed description are exemplary and explanatory only and are not restrictive of the present disclosure, as claimed.

BRIEF DESCRIPTION OF THE DRAWINGS

The accompanying drawings, which are incorporated in and constitute a part of this specification, illustrate various exemplary embodiments and together with the description, serve to explain the principles of the present disclosure.

FIG. 3B depicts a cross-sectional view of the base portion of a basket from FIG. 3A.

FIGS. 11A-D depict graphs of experimental results from an experimental comparison of sperm motility and viability over time between a conventional control container and a container made via three-dimensional printing.

FIGS. 13A-D depict graphs comparing experimental results between a conventional semen analysis and the sample collection system of FIG. 2.

DETAILED DESCRIPTION

Figure 1:
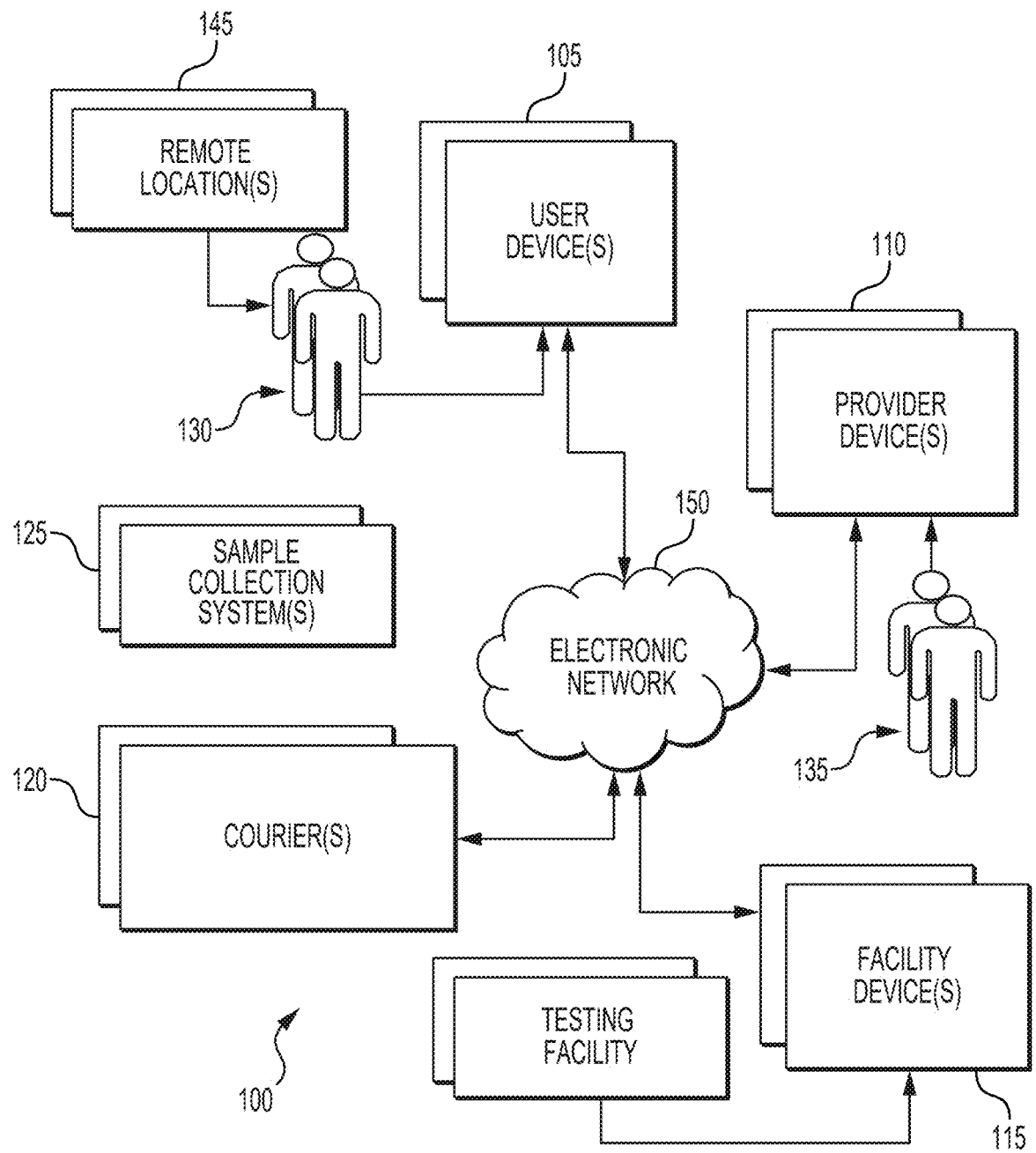
FIG. 1 depicts an exemplary environment for performing male fertility analysis, according to one or more embodiments.

The terminology used below may be interpreted in its broadest reasonable manner, even though it is being used in conjunction with a detailed description of certain specific examples of the present disclosure. Indeed, certain terms may even be emphasized below; however, any terminology intended to be interpreted in any restricted manner will be overtly and specifically defined as such in this Detailed Description section. Both the foregoing general description and the following detailed description are exemplary and explanatory only and are not restrictive of the features, as claimed.

In this disclosure, the term "based on" means "based at least in part on." The singular forms "a," "an," and "the" include plural referents unless the context dictates otherwise. The term "exemplary" is used in the sense of "example" rather than "ideal." The terms "comprises," "comprising," "includes," "including," and other variations thereof, are intended to cover a non-exclusive inclusion such that a process, method, or product that recites a list of elements does not necessarily include only those elements, but may include other elements not expressly listed or inherent to such a process, method, article, or apparatus. Relative terms, such as "substantially," "approximately," and "generally," are used to indicate a possible variation of ±10% of a stated or understood value.

The term "provider" generally encompasses a person and/or entity that facilitates, runs, services, supports, or oversees an activity, e.g., medical care or treatment, laboratory testing, clinical analysis or diagnosis, products or services in support thereof, or the like. A provider may include, for example, one or more of a medical professional, a health institution such as a hospital, a testing facility, etc. In an illustrative example, a fertility doctor may desire that a male patient undergo fertility analysis, and may engage, facilitate, or obtain the services of a testing facility, whereby the testing facility may provide fertility analysis services and/or products, such as via one or more embodiments according to this disclosure.

As noted above, the requirement for a patient to physically travel to a testing facility, either to supply a sample there or drop off a previously prepared sample, may be logistically difficult and/or costly to not only the patient but to the testing facility. Even if the patient is merely dropping off a sample, challenges and logistics of travel may not only decrease accuracy and usability of the sample, but also may increase the logistical burden of the patient due to the strict time window between production and analysis of a sample using conventional solutions.

Thus, improvements to the technology for male fertility analysis may be beneficial. In an exemplary embodiment, systems and methods may be used to obtain motile sperm from a portion of a sample at a location remote from a testing facility, e.g., at a patient's home or any other suitable location. Each of the obtained motile sperm and a remainder of the sample may be sealed and transported to the testing facility, e.g., via courier or the like. The testing facility may determine concentrations of each of the motile sperm and the remainder, and then may apply a predetermined correlation between motile sperm findings and sample remainders to determine one or more characteristics of the sample as a whole, e.g., a total percentage of motile sperm. Such an approach, which does not rely on active, motile sperm at the time of analysis by the testing facility, is resistant to or independent of one or more of time from sample production to delivery at the testing facility, temperature fluctuations during transport, efficacy of buffer media used to transport the sample, etc. Such an approach further provides quantitative data regarding the fertility of the patient.

In an exemplary embodiment, a patient may be provided with a kit. The kit may include, for example, analysis system (such as a fertility analysis system, a first container, a second container, and a loading device. The first container may be a sample container that is configured to receive, for example, a male fertility sample, and that is sealable, e.g., via a removable cap. The second container may include media, e.g., a buffer solution. The analysis system may include a first portion, a second portion, and a porous membrane positioned therebetween. The first portion may be configured to receive an aliquot of a sample received in the first container. With media supplied to the analysis system such that the porous membrane is configured to act as a migration path for motile sperm from the aliquot in the first portion to the media in the second portion, a motile portion of the aliquot may migrate through the porous membrane.

In some embodiments, the first portion may include a chamber with an opening, a concave bottom opposite the opening, and an inlet into the chamber. The porous membrane may extend over the opening, and the second portion may be configured to hold the porous membrane captive (e.g., secured) on or to the first portion.

In some embodiments, the second portion includes a first opening configured to receive the media, and a second opening that is in communication with the first opening and the porous membrane. In an example, the analysis system may have a cup-like shape (e.g., with the first opening having a larger diameter than the second opening), with the porous membrane separating the chamber of the first portion from a remainder of an interior of the cup. A tapered wall between the first opening and the second opening, as well as the sizes of the first and second openings, may facilitate pouring media into and out from the second portion, and may reduce a quantity of media needed to process a sample.

After a predetermined period of time for the motile portion of the aliquot to migrate through the porous membrane, e.g., about an hour at room temperature, the motile portion may be prepared to transport to a testing facility. For example, in some embodiments, the media along with the motile portion of the aliquot may be transferred to the second container, which may be sealed, e.g., with a further cap.

In another exemplary embodiment, a patient may be provided with a kit. The kit may include, for example, a basket, a first container, a second container, a loading device, a supply of media, and/or any other suitable component. The first container may be a sample container that is configured to receive a male fertility sample, and that is sealable, e.g., via a removable cap. The basket includes a chamber covered over by a porous membrane. The patient may use the loading device to load an aliquot of the sample from the first container, and then deposit the aliquot into the chamber using the loading device via an inlet in a base portion of the basket. The patient, e.g., by holding a support structure of the basket, may submerge the base portion and porous membrane of the basket into media disposed in the second container. Over a period of about one hour at room temperature, a portion of motile sperm in the aliquot may migrate through the porous membrane and into the media in the second container at large. The patient may then remove the basket from the second container, e.g., for disposal, and then seal the second container with the migrated motile sperm therein, e.g., via a further cap. The sealed first and second containers may then be transported to a testing facility for analysis.

Thus, system and methods according to one or more embodiments of this disclosure provide a micro-fluidic device suitable for remote, e.g., at-home, use for male fertility analysis that is not subject to risks due to delay in sample delivery, temperature fluctuations, or other challenges subjected to conventional solutions. That is, systems and methods of this disclosure provide a micro-fluidic device for remote, e.g., at-home, use for male fertility analysis that is resistant to and/or independent of factors such as time between sample production and analysis, temperature during transport, efficacy of a buffer used to store the sample, etc.

In the following description, exemplary embodiments of the present disclosure will be described with reference to the accompanying drawings. As will be discussed in more detail below, exemplary systems and methods for male fertility analysis are described. However, it should be understood that the techniques and technologies disclosed herein may be adapted to any suitable activity associated with isolating a motile portion of any suitable sample and performing corresponding analysis thereon. For example, the techniques and technologies disclosed herein may be adapted to one or more aspects of a fertility procedure or for any other suitable activity that incorporates portions of a sample that may diffuse through or be separable via a porous membrane. In an example, such techniques may be applied to sperm selection and/or semen purification, such as may be used for an intrauterine insemination, an in vitro fertilization process, or the like in an assisted reproduction procedure.

FIG. 1 depicts an exemplary environment 100 for providing male fertility analysis. The environment 100 may, in various embodiments, include one or more of a user device 105, a provider device 110, a facility device 115, a courier 120, and a sample collection system 125. The user device 105 may be associated with a patient 130, the provider device 110 may be associated with a provider 135, and the facility device may be associated with a testing facility 140. The patient 130 may be associated with a location 145 that is remote from the testing facility 140.

In some embodiments, the components of the environment 100 are associated with a common entity, e.g., a hospital, doctor's office, medical insurer, or the like. For example, in some embodiments, the testing facility 140 and facility device 115 may be associated with the provider 135 and provider device 110 (e.g., the provider may perform in-house testing/analysis). In some embodiments, one or more of the components of the environment is associated with a different entity than another. The systems and devices of the environment 100 may communicate in any arrangement. As will be discussed herein, systems and/or devices of the environment 100 may communicate and/or cooperate in order to provide male fertility analysis to the patient 130, among other activities.

The user device 105 may be configured to enable the patient 130 to access and/or interact with other devices in the environment 100. For example, the user device 105 may be a computer system such as, for example, a desktop computer, a mobile device, a tablet, etc. In some embodiments, the user device 105 may include one or more electronic application(s), e.g., a program, plugin, browser extension, etc., installed on a memory of the user device 105. In some embodiments, the electronic application(s) may be associated with one or more of the other components in the environment 100. For example, the electronic application(s) may include one or more of a patient medical portal, scheduling application, web browser, etc., which may be configured to interface with programs or services offered by other devices in the environment 100.

In various embodiments, electronic devices in the environment 100, such as the user device 105, provider device 110, etc., may communicate via an electronic network 150, e.g., a local network, the internet, or the like. In some embodiments, one or more systems or devices in the environment may communicate or interact with other systems, such as servers or the like (not shown), e.g., to host, store, retrieve, or process data, as well as other activities.

The provider device 110 may be configured to enable the provider 135 to access and/or interact with other devices in the environment 100. For example, the provider device 110 may be a computer system such as, for example, a desktop computer, a mobile device, a tablet, etc., and may facilitate, schedule, provide, or direct male fertility analysis services offered by the testing facility 140 to the patient 130.

The facility device 115 may be configured to enable the testing facility 140 to access and/or interact with other devices in the environment 100. For example, the facility device 115 may be a computer system such as, for example, a desktop computer, a mobile device, a tablet, etc., and may facilitate communication of analysis results to the provider 135, operations of the courier 120, as well as other activities.

The courier 120 may include a transportation and/or shipping service, e.g., a public mail carrier service, a private direct shipping service, or the like, or a combination thereof. In an example, the courier 120 may provide scheduled or preemptive offering of shipping services, e.g., a shipping label prepared in advance for an item to be delivered.

The sample collection system 125 may include, for example, a device or kit configured to facilitate collection of a male fertility sample from the patient 130 at the location 145 remote from the testing facility. Further aspects of the sample collection system 125 are discussed in more detail below.

Figure 2:
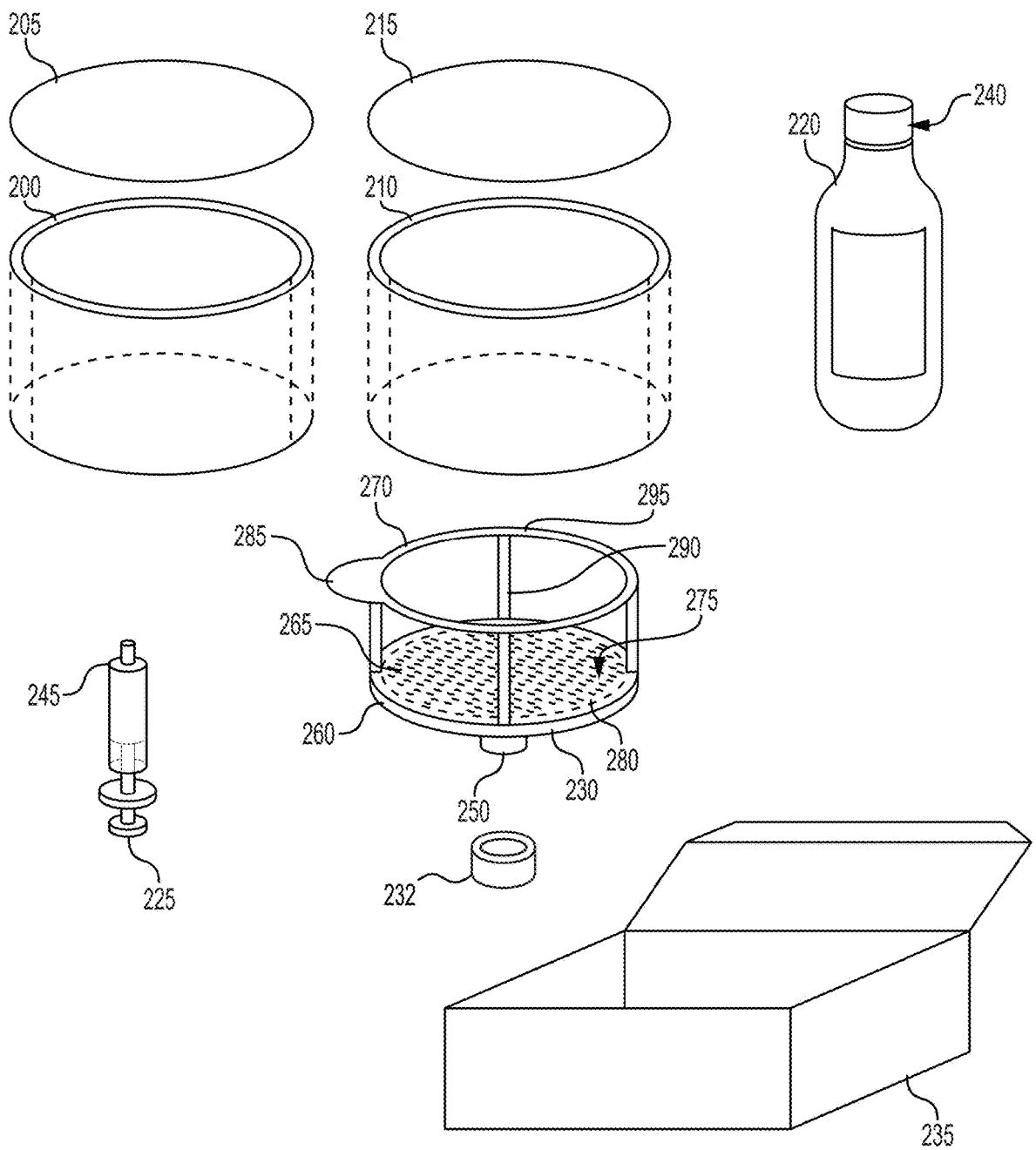
FIG. 2 depicts a perspective view of an exemplary embodiment of a sample collection system from FIG. 1.

FIG. 2 depicts a perspective view of an exemplary embodiment of the sample collection system 125 of FIG. 1. In this embodiment, the sample collection system 125 is provided as a kit, e.g., a collection of various components. However, in various embodiments, the sample collection system 125 or components thereof may be provided separately or in any suitable combination or arrangement. As depicted in FIG. 2, the sample collection system 125 includes a first container 200, a first cap 205, a second container 210 that holds a media supply, a second cap 215, a loading device 225, a basket 230, an inlet cap 232, and a transport case 235.

The first cap 205 may be configured to removably seal the first container 200 in any appropriate manner (e.g., via threaded engagement, etc.). The first container 200 may be a container for receiving a male fertility sample. In some embodiments, the first container 200, may be empty or otherwise devoid of media. The second cap 215 may be configured to removably seal the second container 210 in any appropriate manner (e.g., via threaded engagement, etc.). The second container 210 may be a container configured to receive at least a portion of the basket 230 such that the portion is submerged in media 240, as discussed in further detail below. In some embodiments, the second container 210, e.g., when supplied with the kit, is pre-filled with media 240. The media supply 220 may include media 240, e.g., to initially supply the second container 210 and/or provide a reserve. In some embodiments, e.g., some embodiments in which the second container is pre-filled, the media supply may not be included with the kit. In various embodiments, the media 240 may include, for example, a saline solution, a sperm wash solution, a protein-enriched solution, any suitable sperm survival buffer, or combinations thereof.

The loading device 225 may be operable to obtain and load a portion of a male fertility sample. In an exemplary embodiment, the loading device 225 may be graduated and/or sized to obtain an aliquot (e.g., a portion separated from the sample) of about 1 mL from a male fertility sample. Any suitable type of loading device may be used. In some embodiments, the loading device 225 may include a nozzle 245 matched to an inlet 250 of the basket 230, as discussed in further detail below. In various embodiments, the loading device 225 may include, for example, a syringe, a transfer pipette, a Pasteur pipette, a scoop, a swab, etc.

The basket 230 includes a base portion 260, a porous membrane 265, and a support structure 270. The base portion 260 includes a chamber 275 with an opening 280, and the inlet 250 that opens into the chamber 275. In some embodiments, the chamber 275 includes a rounded or concave bottom, such as an example discussed in further detail below with regard to FIG. 3B. As noted above, in some embodiments, the inlet 250 has a size and/or shape matched to a size and/or shape of an outlet of the loading device 225. The inlet 250 enables operation of the loading device 225 to load an aliquot from a male fertility sample into the chamber 275. In this embodiment, the inlet 250 is oriented substantially vertically with the basket 230, e.g., relative to a plane of the porous membrane 265. However, in various embodiments, the inlet 250 may be at various orientations, as discussed in further detail below.

The inlet cap 232 is configured to close off the inlet 250. In an example, the inlet cap 232 is configured to have a removable fit with an interior shape of the inlet 250. In some embodiments, the inlet cap 232 is configured such that once installed in the inlet 250, the inlet cap 232 is not or is not readily graspable or removable. In some embodiments, the inlet cap 232 is configured to be non-removable.

The support structure 270 extends vertically up from the base portion 260. The support structure 270 is configured such that, with the basket 230 received in the second container 210, at least a portion of the support structure is graspable, e.g., by the patient 130, to facilitate installation and removal of the basket 230 from the second container. In some embodiments, the support structure 270 includes a grip portion 285 configured to facilitate grasping the support structure 270. In this embodiment, the grip portion 285 includes a tab, e.g., that is configured to hang over a rim of the second container 210 when the basket 230 is disposed therein. In some embodiments, no grip portion is included.

In this embodiment, the support structure 270 includes a plurality of struts 290 that are distributed about an outer border of the porous membrane and connected together via a top annulus 295. However, any suitable configuration or arrangement of the support structure may be used in various embodiments. In an example, the support structure may include, instead of or in addition to the struts 290, a central support that is configured to extend from an outer border of the base portion toward a center of the porous membrane and then up and out from the second container 210 (e.g., with a shape similar to a tea diffusor). In some embodiments, the support structure 270 is configured to one or more of locate or stabilize the basket 230 relative to the second container 210.

The porous membrane 265 closes off the opening 280 of the chamber 275, and is positioned between the base portion 260 and the support structure 270. In this embodiment, the porous membrane 265 is a membrane with 10 μm diameter pores. However, in various embodiments, any suitable membrane or the like that permits passage of motile sperm may be used.

In some embodiments, the basket 230 is configured to be disposable, e.g., is formed at least substantially from material that is low cost, facilitates manufacture, is bio-degradable, etc.

The transport case 235 is configured to receive the first container 200 and second container 210, e.g., sealed via the first cap 205 and second cap 215, respectively. In some embodiments, the transport case 235 may include a packing structure, e.g., having a shape matched to and configured to receive the first container 200 and second container 210. Any suitable packing structure may be used. In some embodiments the transport case 235 may be provided with or may include pre-applied transportation information, e.g., a prepared shipping slip or the like associated with the courier 120. In some embodiments, one or more of the first container 200, second container 210, or the transport case 235 may include or be provided with iconography or labeling uniquely associated with the patient 130. In an example, one or more of the foregoing elements may include a scan-able code such as a barcode or QR code usable by one or more of the provider 135, the testing facility 140 or the like, e.g., in order to maintain an identification and association of the sample collection system 125 with the patient 130, to track transportation of the sample collection system 125, and/or to associate analysis results with the patient 130 and/or a patient medical profile of the provider 135.

Figure 3A:
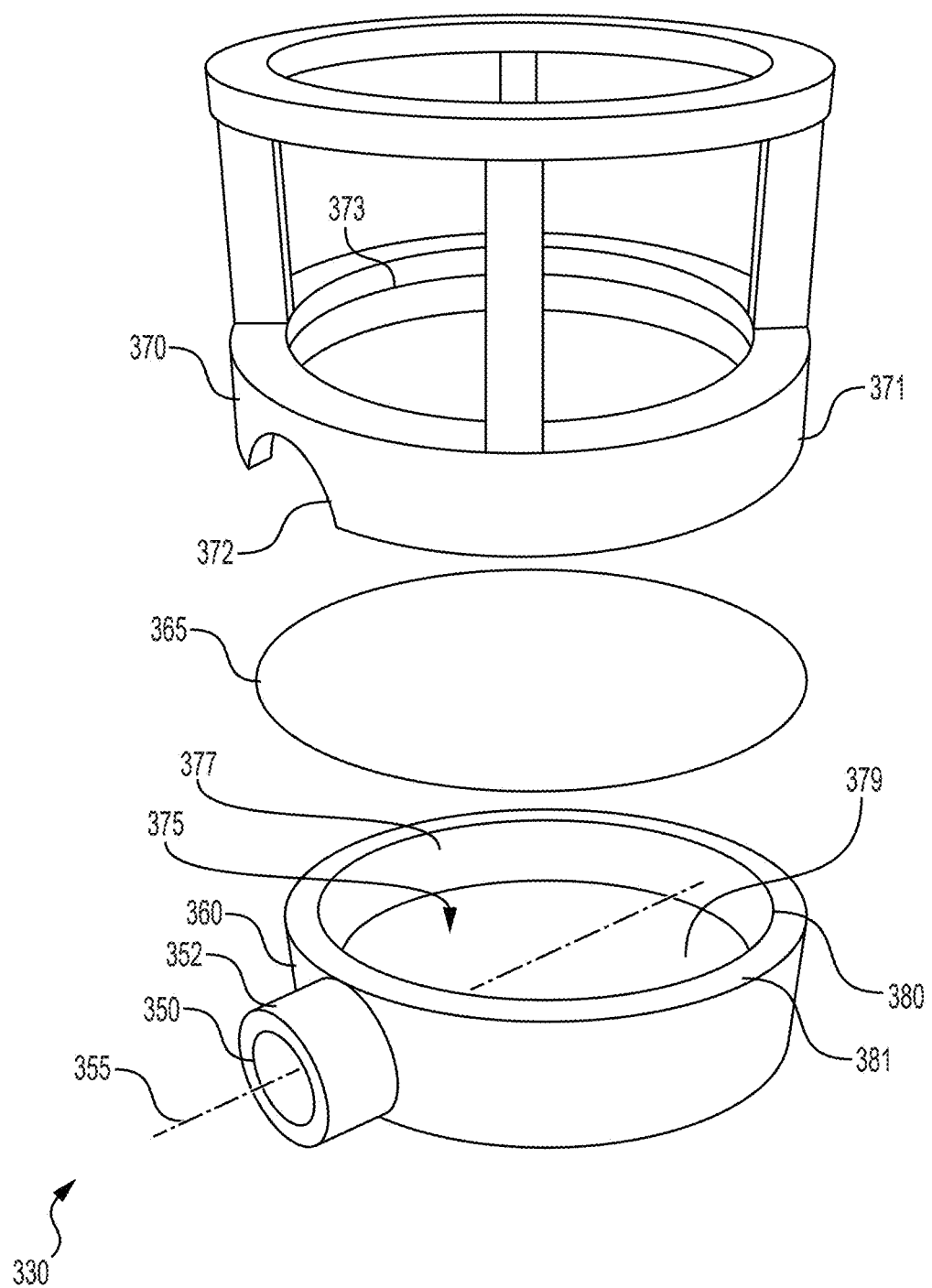
FIG. 3A depicts an exploded view of another exemplary embodiment of a sample collection system from FIG. 1.

FIG. 3A depicts an exploded view of an exemplary embodiment of a basket 330 according to this disclosure. Unless indicated otherwise, elements of the basket with similar reference numerals are similar elements with similar features. Similar to the basket 230, the basket 330 depicted in FIG. 3A includes a base portion 360, a porous membrane 365, and a support structure 370. The base portion 360 includes a chamber 375 and an inlet 350 that opens into the chamber 375. The chamber 375 is defined by a wall 377, a base 379, and an opening 380.

In this embodiment, the inlet 350 is oriented such that an axis 355 of the inlet does not intersect with the porous membrane 365. In other words, the inlet 350 may be oriented such that an aliquot of a sample loaded into the chamber 375 via the inlet 350 is not loaded in a direction of the porous membrane 365. In some instances, such as when the loading device 225 is operated forcefully, a portion of the aliquot may impact directly on the porous membrane 365, with a result that some of that portion may pass through the porous membrane 365 at least partially due to the force of the loading instead of due to migration of the sperm. With the inlet 350 oriented as discussed above, e.g., so that a forceful loading of the chamber 375 is directed to the wall 377 and/or the base 379, such issues may be inhibited, reduced, prevented, or otherwise ameliorated. As depicted in FIG. 3, the inlet 350 includes a neck portion 352 that extends out from the wall 377. As discussed in further detail below, the neck portion 352 may have a shape matched to a portion of the support structure 370 and/or an internal cross-section (e.g., a diameter) configured to cooperate with a cross-section of the outlet of the loading device 225.

In this embodiment, the wall 377 includes a surface 381, e.g., an outer rim, that surrounds the opening 380 and that is configured to support the porous membrane 365.

The support structure 370 includes a wall 371 configured to fit about the wall 377 of the base portion 360. The wall 371 of the support structure 370 includes a collar portion 372, e.g., a cutout or portion shaped to match with and/or receive the neck portion 352 of the inlet 350. Additionally, the wall 371 includes a lip 373 that, with the support structure 370 disposed on the base portion 360, holds the porous membrane 365 captive (e.g., secured) against the surface 381 of the wall 377. In some embodiments, the wall 371 and the wall 377 may be configured to form a snap fit with each other. In some embodiments, a binding agent, such as a glue, epoxy, sealant, or the like may be used to affix one or more of the base portion 360, porous membrane 365, or support structure 370 with each other. For example, in an embodiment, a double-sided adhesive tape is applied. In an embodiment, a double-sided adhesive tape is cut and/or formed into a first and second ring-like shape (e.g., a shape corresponding to an outer contour of the base portion 360 and having a central opening corresponding to the opening 380). Each portion of the double-sided adhesive is affixed to a respective side of the porous membrane 365, such that when the porous membrane 365 is situated between the base portion 360 and the support structure 370, the double-sided adhesive portions are affixed thereto, respectively. It should be understood that the foregoing arrangement is exemplary only, and that any suitable arrangement or procedure with a double-sided adhesive and/or any other suitable fixing agent may be used. In some embodiments, the fixing of elements, e.g., as discussed in the foregoing example, is configured to form a seal between the respective elements, e.g., to inhibit escape of media and/or portions of the aliquot.

In some embodiments, the chamber 375 is configured with a smoothed or rounded shape, e.g., to soften, reduce, and/or eliminate edges or creases between surfaces of the chamber 375. For example, in some embodiments, the wall 377 of the chamber 375 may include a rounded transition to a bottom of the chamber 375. FIG. 3B depicts a cross-section view of the base portion 360. As depicted in FIG. 3B, the chamber 375 includes a bottom 376 having a concave shape. The concave shape of the bottom 376 of the chamber 375 may facilitate the introduction of the aliquot into the chamber 375, may promote the migration of motile sperm, and/or may reduce an impact of an overly forceful operation of the loading device 225. In an example, a rounded shape for the chamber 375 such as the concave shape of the bottom 376 may one or more of act as a guide for motile sperm, e.g., that leads motile sperm toward the porous membrane 365. In an example, reducing or eliminating edges or creases, such as by including a rounded transition between the wall 377 and bottom 376 of the chamber 375 and/or other surfaces may reduce or inhibit a portion of a sample from being trapped therein.

In some embodiments, at least a portion of the basket 330 is formed via a three-dimensional printing process. In an example, a stereolithography three-dimensional printing device (not shown) may be employed, e.g., in which a piece is assembled layer-by-layer by successively exposing layers of a photosensitive polymer to light. In an example, a vertically movable base steps away from a screen submerged in photosensitive polymer. The screen outputs light to which the photosensitive polymer is sensitive, e.g., ultraviolet light, in a pattern corresponding to a respective layer for each step. In some instances, once a piece has been printed, e.g., via the foregoing process, the piece may be subjected to a curing process. In an example, a piece may be exposed to ultraviolet light, e.g., for an hour or more, to more fully cure the photosensitive polymer of the piece. Such curing may improve a biocompatibility of the piece, may improve an inter-layer sealing of the piece, etc. In various embodiments, any suitable post-printing processing may be used, e.g., acid-etching, smoothing, washing, coating, etc. Any suitable photosensitive polymer may be used for stereolithography three-dimensional printing, and any suitable resin or material or combination may be used for other three-dimensional printing techniques.

However, in various embodiments, any suitable manufacturing and/or assembly process may be used. Any suitable material or combination of materials may be used for the various elements of the basket 330, and for the kit as a whole.

Figure 4:
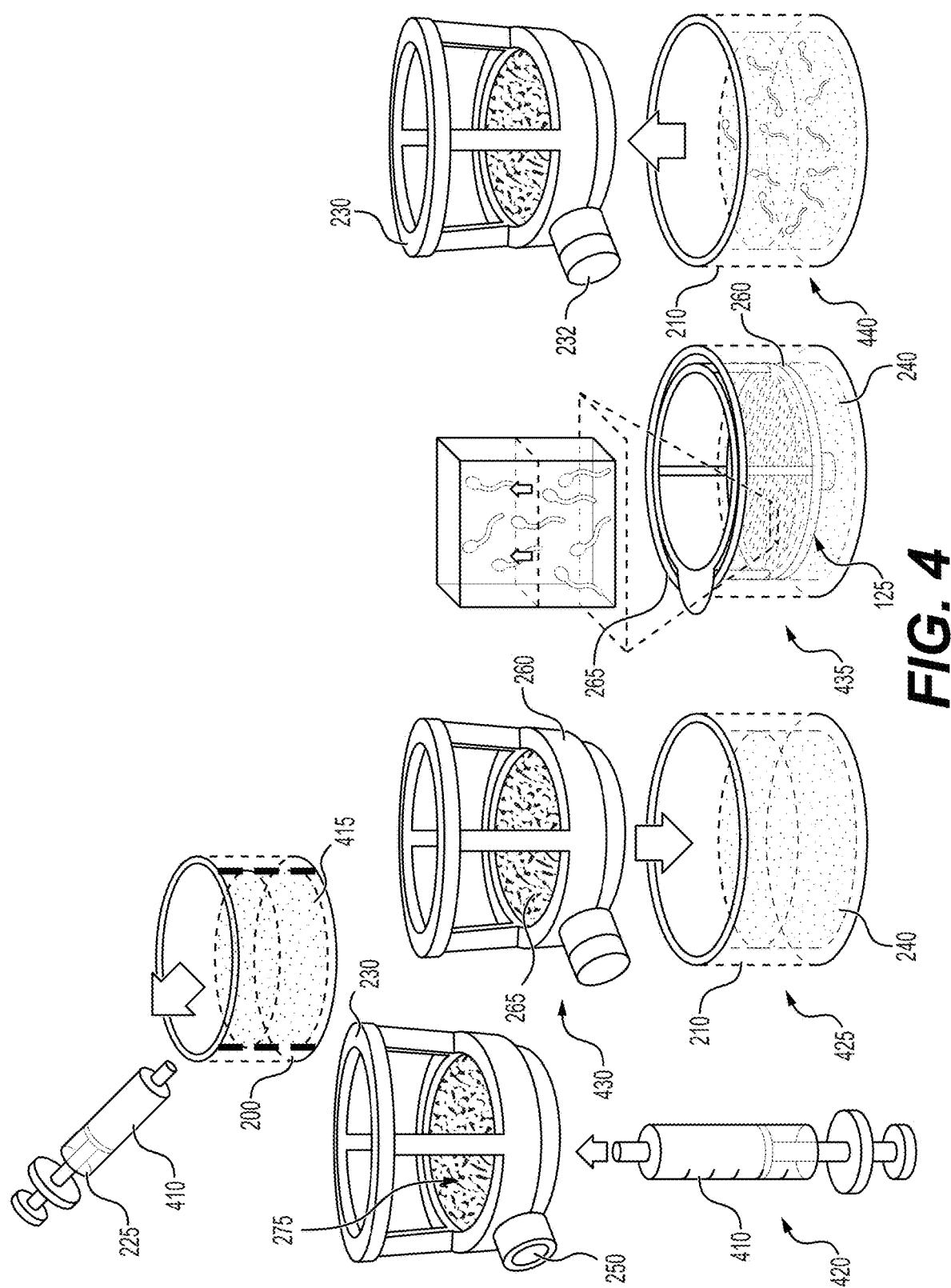
FIG. 4 depicts a flow diagram of an exemplary process for operation of the sample collection system from FIG. 1.

FIG. 4 illustrates an operational flow 400 for using the sample collection system 125. At step 405, the loading device 225 is operated to load an aliquot 410 (e.g., about 1 mL) of a male fertility sample 415 from the first container 200. At step 420, the aliquot 410 is loaded via the inlet 250 into the chamber 275 of the basket 230. Optionally, at step 425, media 240 (e.g., about 10 mL) is supplied to the second container 210. It should be understood that, in some embodiments, the second container 210 may be provided with media 240 already present therein. At step 430, an inlet cap 232 is applied to close off the inlet 250, and the basket 230 is inserted into the second container 210 such that the base portion 260 and porous membrane 265 are submerged in the media 240. At step 435, the sample collection system 125 is kept at room temperature for about one hour. During this period of time, motile sperm from the aliquot 410 migrate through pores of the porous membrane 265 into the media 240. At step 440, the basket 230, along with the remainder of the aliquot 410, e.g., non-motile sperm, dead sperm, or sperm that failed to migrate, is removed from the second container 210. At step 445, the first cap 205 is used to seal the first container 200 and the second cap 215 is used to seal the second container 210. At step 450, the first container 200 and second container 210 are loaded into the transport case 235 for transport to the testing facility 140, e.g., via the courier 120.

Figure 5:
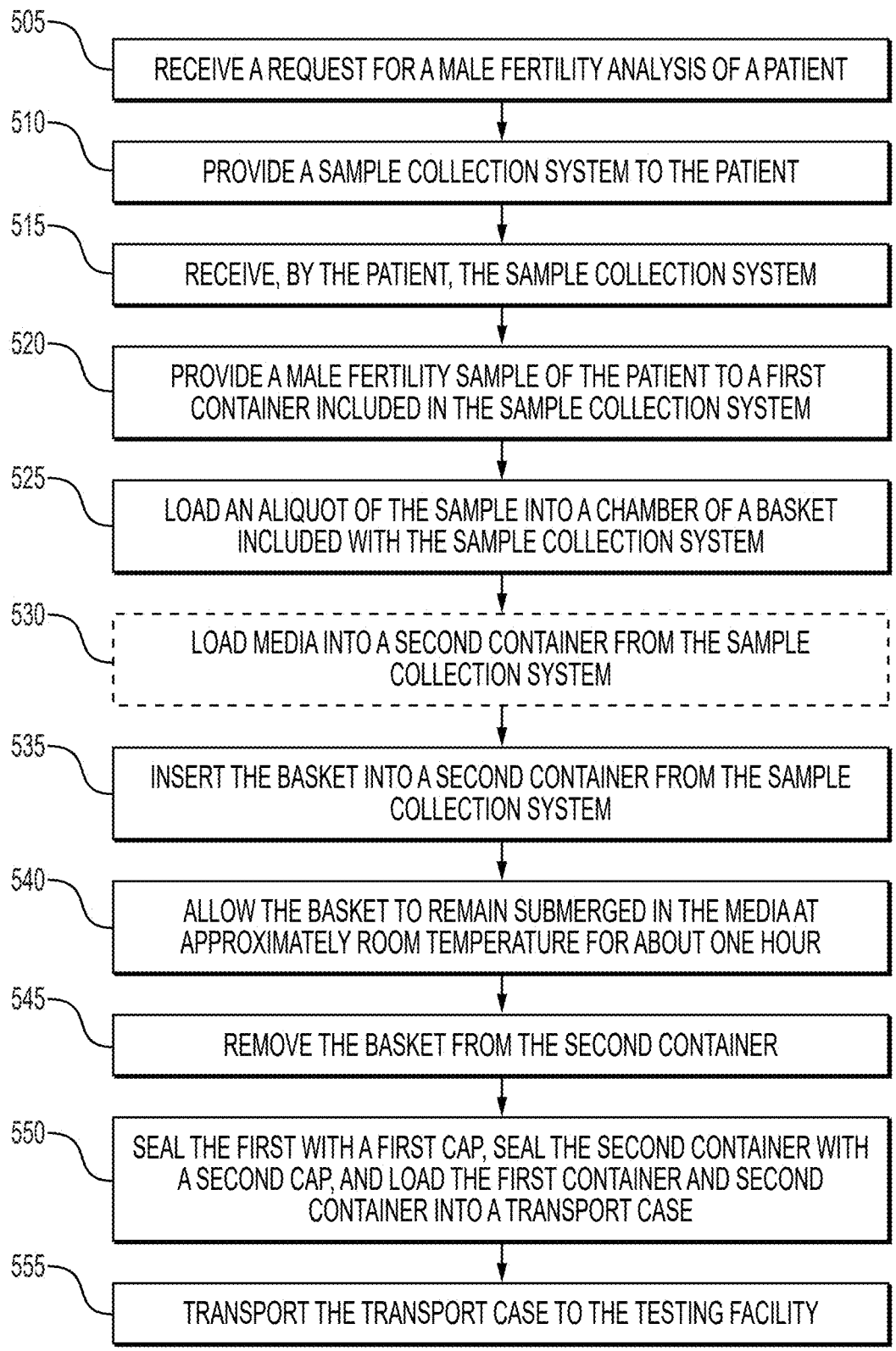
FIG. 5 depicts a flow diagram of an exemplary embodiment of collecting a male fertility sample using a sample collection system, according to one or more embodiments.

FIG. 5 is a flow diagram illustrating an exemplary embodiment of a method for collecting a male fertility sample via a sample collection system 125. At step 505, a facility device 115 of a testing facility 140 may receive a request for a male fertility analysis of a patient 130. In various embodiments, the request is received from a provider 135 via a provider device 110, from the patient 130 via a user device 105, etc. At step 510, the testing facility 140 may provide a sample collection system 125 to the patient 130. In some embodiments, the sample collection system 125 may be provided as a kit. In various embodiments, sample collection system 125 may be provided via the provider 135 (e.g., during a patient visit), via the courier 120 (e.g., as a delivery to a location 145 associated with the patient 130 such as their home address), or the like. In some embodiments, the testing facility may generate a unique identifier associating the sample collection system 125 with the patient 130 and/or the provider 135, and may include or affix a label or other indication of the unique identifier with the sample collection system 125. In some embodiments, the testing facility 140 may register the sample collection system 125 with a medical data system associated with the provider 135, or the like.

At step 515, the patient 130 may receive the sample collection system 125. At step 520, the patient 130 may provide a male fertility sample to a first container 200 included in the sample collection system 125. At step 525, the patient 130 may load an aliquot of the sample into a chamber 275 of a basket 230 included with the sample collection system, e.g., via a loading device 225 and into an inlet 250 in a base portion 260 of the basket 230. Optionally at step 530, the patient 130 may load media 240 into a second container 210 from the sample collection system 125, e.g., from a media supply 220.

At step 535, the patient 130, e.g., by gripping a support structure 270 of the basket 230 such as a grip portion 285, may insert the basket 230 into a second container 210 from the sample collection system 125 such that the base portion 260 and a porous membrane 265 extending over an opening in the chamber 275 are submerged in media disposed in the second container 210, and such that an interface is formed between the aliquot, the porous membrane 265, and the media 240.

At step 540, the patient 130 may allow the basket 230 to remain submerged in the media 240 at approximately room temperature for about one hour, during which at least a portion of motile sperm from the aliquot may migrate through pores of the porous membrane 265 and into the media 240. At step 545, the patient 130 may remove the basket 230 from the second container 210, e.g., via manipulating the support structure 270. At step 550, the patient 130 may seal the first container 200 (with a remainder of the male fertility sample therein) with a first cap 205, may seal the second container (with the portion of motile sperm that migrated through the porous membrane 265 into the media 240 therein) with a second cap 215, and may load the first container 200 and second container 210 into a transport case 235. At step 555, the patient 130 may transport the transport case 235 to the testing facility 140, e.g., via the courier 120.

Figure 6:
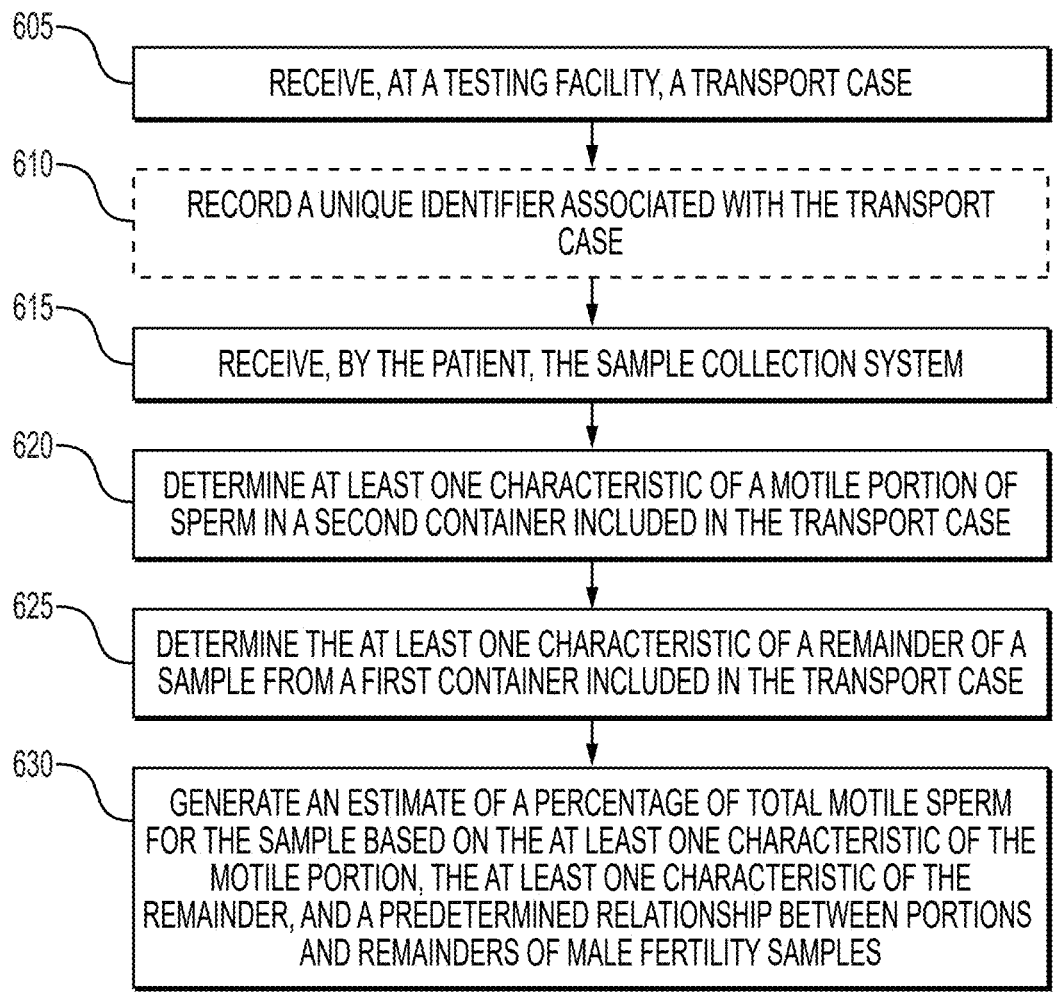
FIG. 6 depicts a flow diagram of an exemplary embodiment of performing analysis of a male fertility sample collected using a sample collection system, according to one or more embodiments.

FIG. 6 is a flow diagram illustrating an exemplary embodiment of a method for analyzing a male fertility sample collected via a sample collection system 125. At step 605, a testing facility may receive, e.g., via a courier 120, a transport case 235. The transport case 235 may include, for example, a first container 200 including a remainder of a male fertility sample, and a second container 210 including a motile portion of an aliquot from the male fertility sample in media 204, e.g., as collected via the method 500 discussed above with regard to FIG. 5. In some embodiments, one or more of the transport case 235, the first container 200, or the second container 210 may include a unique identifier associated with a patient 130. Optionally, at step 610, the testing facility 140, e.g., via a facility device 115, may scan or otherwise enter the unique identifier, e.g., in order to associate the sample collection system 125 with one or more of the patient 130 (e.g., via a patient medical data storage), a provider 135 (e.g., via an interface with a provider device 110), or the like. At step 615, the testing facility 140 may determine at least one characteristic of the motile portion of the sperm in the second container 210. In various embodiments, the at least one characteristic may include, for example, one or more of concentration (e.g., million sperm per mL of sample), quantity, volume, or any other suitable characteristic associated with male fertility. Any suitable technique may be used. In an example, a Makler counting chamber may be employed to determine a count of sperm of an input portion or sample. For example, a portion, e.g., about 5 µL, of a sample is introduced into a Makler counting chamber, and then is observed under a microscope in order to take a count. The count may then be extrapolation to the sample as a whole. At step 620, the testing facility 140 may determine the at least one characteristic of the remainder of the sample from the first container 200. At step 625, the testing facility may generate an estimate of a percentage of total motile sperm for the male fertility sample based on the at least one characteristic of the motile portion, the at least one characteristic of the remainder, and a predetermined relationship between portions and remainders of male fertility samples.

In an example, the predetermined relationship may include a correlation coefficient that relates (i) a concentration of sperm (e.g., count per volume) in a motile portion of a sample (e.g., the characteristic determined for the portion collected in the second container 210 of the sample collection system 125) to (ii) a concentration of motile sperm in a sample as a whole. Experimentation of 50 tests in which, in each case a motile portion and remainder were collected as per the procedure discussed above with regard to FIG. 5, resulted in a coefficient of about 10, with a standard deviation between tests of about 5, whereby $$K \times \text{motile portion concentration} = \text{concentration of motile sperm in a total sample}$$

in which K is the correlation coefficient. In this manner, an estimate for the concentration of motile sperm in a total sample may be generated given the determined concentration of the motile portion collected in the second container 210. Then, the total concentration of the remainder (e.g., the characteristic determined for the remainder in the first container 200) may be used to estimate a percentage of the total sample that is motile, whereby:

$$\% \text{ motility of total sample} = \frac{\text{concentration of motile sperm in a total}}{\text{concentration of the remainder}}$$

Thus, the percentage of motile sperm in a sample may be estimated using the concentration of the extracted motile portion, the concentration of the remainder, and the correlation coefficient K.

In an exemplary embodiment, the second container 210 may include and/or be compatible with a loading mechanism (not shown) that is operable to guide and/or load the basket 230 into and/or out from the second container 210, e.g., in an at least partially guided and/or automated fashion. In an example, a loading mechanism may include a winch mechanism, an actuator, a solenoid, or the like, that is operable to move the basket 230 into and out from the second container 210. In some embodiments, the loading mechanism may include and/or be configured to operate with or based on a remote device (e.g., a mobile device configured to send operation instructions), a timer (e.g., for setting entry and removal points for the basket 230 to allow exposure of a sample loaded into the basket 230 to the media 240 for a predetermined period of time), etc. The loading mechanism may, in various embodiments, include a power source such as a battery, a power connection port, etc. In some embodiments, the loading mechanism may be manually operable by a user, e.g., by a crank shaft, wheel, or the like.

Figure 7:
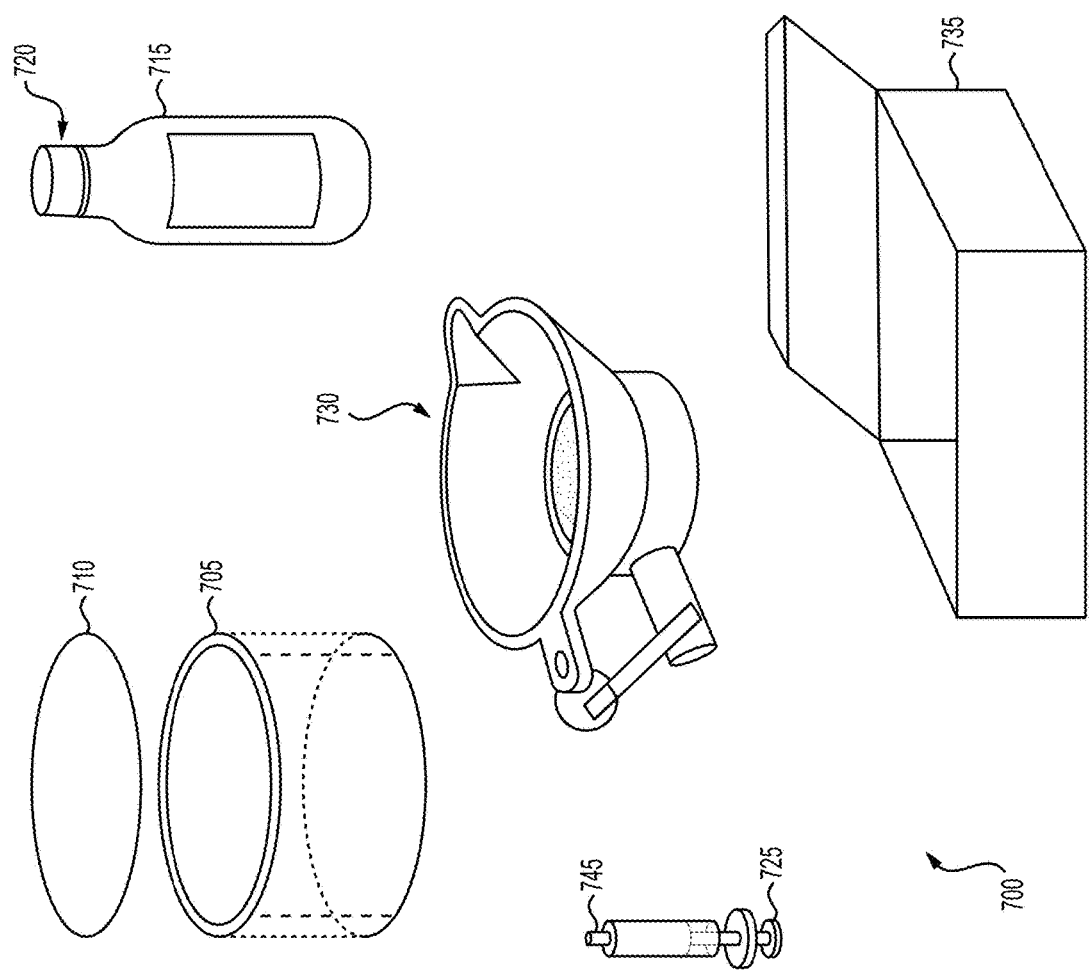
FIG. 7 depicts a perspective view of exemplary embodiment of a sample collection kit, according to one or more embodiments.

FIG. 7 depicts a perspective view of another exemplary embodiment of a sample collection system 700. In this embodiment, the sample collection system 700 is provided as a kit, e.g., a collection of various components. However, in various embodiments, the sample collection system 700 or components thereof may be provided separately or in any suitable combination or arrangement. As depicted in FIG. 7, the sample collection system 700 includes a first container 705, a first cap 710, a second container 715 that holds a media supply, a second cap 720, a loading device 725, an analysis system 730 (e.g., a fertility analysis system), and a transport case 735.

The first cap 710 may be configured to removably seal the first container 705 in any appropriate manner (e.g., via threaded engagement, etc.). The first container 705 may be a container for receiving a male fertility sample. In some embodiments, the first container 705 may be empty or otherwise devoid of media. The second cap 720 may be configured to removably seal the second container 715 in any appropriate manner (e.g., via threaded engagement, etc.). As noted above, the second container 715 may include a supply of media, e.g., a buffer solution or the like. In various embodiments, the media may include, for example, a saline solution, a sperm wash solution, a protein-enriched solution, any suitable sperm survival buffer, or combinations thereof.

The loading device 725 may be operable to obtain and load a portion of a male fertility sample, e.g., from the first container 705. In an exemplary embodiment, the loading device 725 may be graduated and/or sized to obtain an aliquot (e.g., a portion separated from the sample) of about 1 mL from a male fertility sample. Any suitable type of loading device may be used. In some embodiments, the loading device 725 may include a nozzle 745 matched (e.g., sized or configured to correspond) to an inlet of the analysis system 730, as discussed in further detail below. In various embodiments, the loading device 725 may include, for example, a syringe, a transfer pipette, a Pasteur pipette, a scoop, a swab, etc.

As discussed in further detail below, the analysis system 730 may be configured to separate a motile portion of sperm from the aliquot of the male fertility sample. In some embodiments, the analysis system 730 is configured to be disposable, e.g., is formed at least substantially from material that is low cost, facilitates manufacture, is bio-degradable, etc. In some embodiments, at least a portion of the analysis system 73 may be formed using three-dimensional printing techniques. Such techniques may facilitate rapid manufacturing and, as discussed in further detail below, do not interfere with the quality of analysis provided by the analysis system 730.

The transport case 735 is configured to receive the first container 705 and second container 715, e.g., sealed via the first cap 710 and second cap 720, respectively. In some embodiments, the transport case 735 may include a packing structure, e.g., having a shape matched to and configured to receive the first container 705 and second container 715. Any suitable packing structure may be used. In some embodiments the transport case 735 may be provided with or may include pre-applied transportation information, e.g., a prepared shipping slip or the like associated with the courier 120. In some embodiments, one or more of the first container 705, second container 715, or the transport case 735 may include or be provided with iconography or labeling uniquely associated with the patient 130. In an example, one or more of the foregoing elements may include a scan-able code such as a barcode or QR code usable by one or more of the provider 135, the testing facility 140 or the like, e.g., in order to maintain an identification and association of the sample collection system 125 with the patient 130, to track transportation of the sample collection system 125, and/or to associate analysis results with the patient 130 and/or a patient medical profile of the provider 135.

Figure 8:
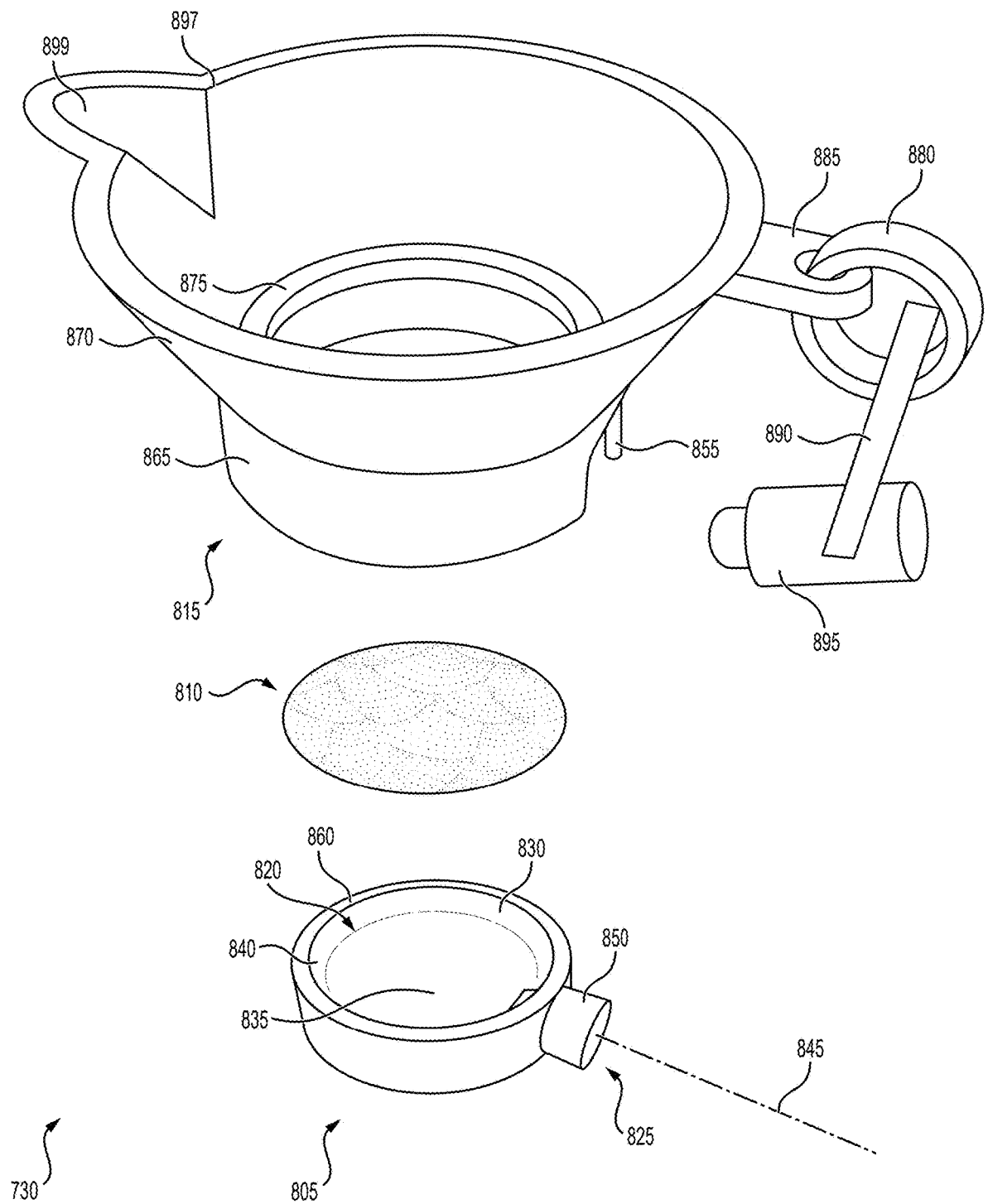
FIG. 8 depicts an exploded view of an analysis system from the kit of FIG. 7.

FIG. 8 depicts an exploded view of an exemplary embodiment of the analysis system 730, according to this disclosure. As depicted in FIG. 8, the analysis system 730 includes a first portion 805, a porous membrane 810, and a second portion 815.

The first portion 805 includes a chamber 820 and an inlet 825 that opens into the chamber 820. The chamber 820 is defined by a wall 830, a bottom 835, and an opening 840.

In this embodiment, the inlet 825 is oriented such that an axis 845 of the inlet does not intersect with the porous membrane 810 in an assembled position of the analysis system 730. In some embodiments, the axis 845 may be parallel or substantially parallel with a plane along which the porous membrane 810 extends. In other words, the inlet 825 may be oriented such that an aliquot of a sample loaded into the chamber 820 via the inlet 825 is not loaded directly toward the porous membrane 810. As depicted in FIG. 8, the inlet 825 includes a neck portion 850 that extends out from the wall 830. As discussed in further detail below, the neck portion 850 may have a shape matched to a collar 855 of the second portion 815 and/or an internal cross-section (e.g., a diameter) configured to cooperate with a cross-section of the outlet of the loading device 725.

In this embodiment, the wall 830 includes a surface 860, e.g., an outer rim, that surrounds the opening 840 and that is configured to support the porous membrane 810.

In some embodiments, the chamber 820 is configured with a smoothed or rounded shape, e.g., to soften, reduce, and/or eliminate edges or creases between surfaces of the chamber 820. For example, in some embodiments, the wall 830 of the chamber 820 may include a rounded transition to a bottom 835 of the chamber 820. In an example, a concave shape of the bottom 835 of the chamber 820 may facilitate the introduction of the aliquot into the chamber 820, may promote the migration of motile sperm, and/or may reduce an impact of an overly forceful operation of the loading device 725. In an example, a rounded shape for the chamber 820 such as the concave shape of the bottom 835 may one or more of act as a guide for motile sperm, e.g., that leads motile sperm toward the porous membrane 810. In an example, reducing or eliminating edges or creases, such as by including a rounded transition between the wall 830 and bottom 835 of the chamber 820 and/or other surfaces may reduce or inhibit a portion of a sample from being trapped therein.

The porous membrane 810 closes off the opening 840 of the chamber 820, and is positioned between the first portion 805 and the second portion 815. In this embodiment, the porous membrane 810 is a membrane with approximately 10 µm diameter pores. However, in various embodiments, any suitable membrane or the like that permits passage of motile sperm or another sample of interest may be used.

The second portion 815 includes a first wall 865, a second wall 870, a lip 875, and an inlet cap 880. The first wall 865 is configured to fit around the wall 830 of the first portion 805. The first wall 865 includes the collar 855 that is configured to fit around the neck portion 850 of the inlet 825 of the first portion 805.

In some embodiments, a bottom surface of the lip 875 is configured to engage the surface 860 of the wall 830 of the first portion 805. In an example, the lip 875 may act as a stop to locate the first portion 805 within the first wall 865 of the second portion 815. In some embodiments, the first wall 865 and the wall 830 may be configured to form a snap fit with each other. In some embodiments, a binding agent, such as a glue, epoxy, sealant, or the like may be used to affix one or more of the first portion 805, porous membrane 810, or second portion 815 with each other. It should be understood that the foregoing arrangement is exemplary only, and that any suitable arrangement or procedure with a double-sided adhesive and/or any other suitable fixing agent may be used. In some embodiments, the fixing of elements, e.g., as discussed in the foregoing example, is configured to form a seal between the respective elements, e.g., to inhibit escape of media and/or portions of the aliquot. In an embodiment, the first and second portions may be integral with each other, with the porous membrane affixed thereto via the lip, or the like.

In some embodiments, a top surface of the lip 875 or another similar structure may be configured to act as a fill line for media in analysis system 730, as discussed in further detail below. As such, one or more portions of the analysis system 730 (e.g., lip 875) may include indicia, instructions, text, depictions, or the like embedded or otherwise positioned thereon to guide a user to fill the analysis system 730 to the identified level or line.

In this embodiment, the inlet cap 880 is attached to the second portion 815. For example, the inlet cap 880 may include a first fixed portion 885 and a second movable portion 890. The fixed portion 885 may be integral to or affixed on the second wall 870, and the movable portion 890 may be movably attached to the fixed portion 885. In this embodiment, the movable portion 890 has a ring or the like chained on to a ring of the fixed portion. However, any suitable movable connection may be used. The movable portion 890 includes a plug 895 configured to seal off the inlet 825 of the first portion 805. In some embodiments, the plug 895 is configured so as to be non-removable. In an example, the plug 895 may be configured such that a substantial portion or all of the plug 895 is received in the inlet 825 (e.g., to reduce a graspable portion that would be used to remove the plug 895). In another example, the plug 895 may be configured such that a force to remove the plug 895 from the inlet 825 (e.g., by grasping the movable portion 890) exceeds a strength of the movable portion 890 so that a graspable portion of the movable portion 890 snaps off from the plug 895 before the plug 895 is removed. In some embodiments, the plug 895 is configured to have a removable fit with an interior shape of the inlet 825.

The second wall 870, in this embodiment, includes a cup or funnel-like shape, e.g., such that, in an assembled position, a first opening 897 of the second portion 815 is in communication with the porous membrane 810 and with the chamber 820 there-through. In some embodiments, the second wall 870 decreases in diameter e.g., tapers, in a direction away from the first opening 897. In other words, the first opening 897 may have a diameter that is larger than a diameter at which the second portion 815 meets the porous membrane 810, e.g., the cup shape of the second portion narrows toward the bottom. Such a narrowing shape may facilitate pouring media into and out from the second portion 815, may direct media introduced to the second portion 815 toward the porous membrane 810, and may reduce a quantity of media needed to saturate the porous membrane 810.

In this embodiment, the second wall 870 includes a spout 899 configured to facilitate removal, e.g., pouring out, of material from out of the analysis system 730, as discussed in further detail below.

In some embodiments, at least a portion of the analysis system 730 is formed via a three-dimensional printing process. However, in various embodiments, any suitable manufacturing and/or assembly process may be used. Any suitable material or combination of materials may be used for the various elements of the analysis system 730, and for the kit as a whole.

It should also be understood that the embodiment discussed above with regard to FIGS. 7 and 8 is exemplary only. Any suitable structure for providing a porous membrane to separate off a chamber from a further interior portion of the structure so that motile sperm may migrate through may be used.

Figure 9:
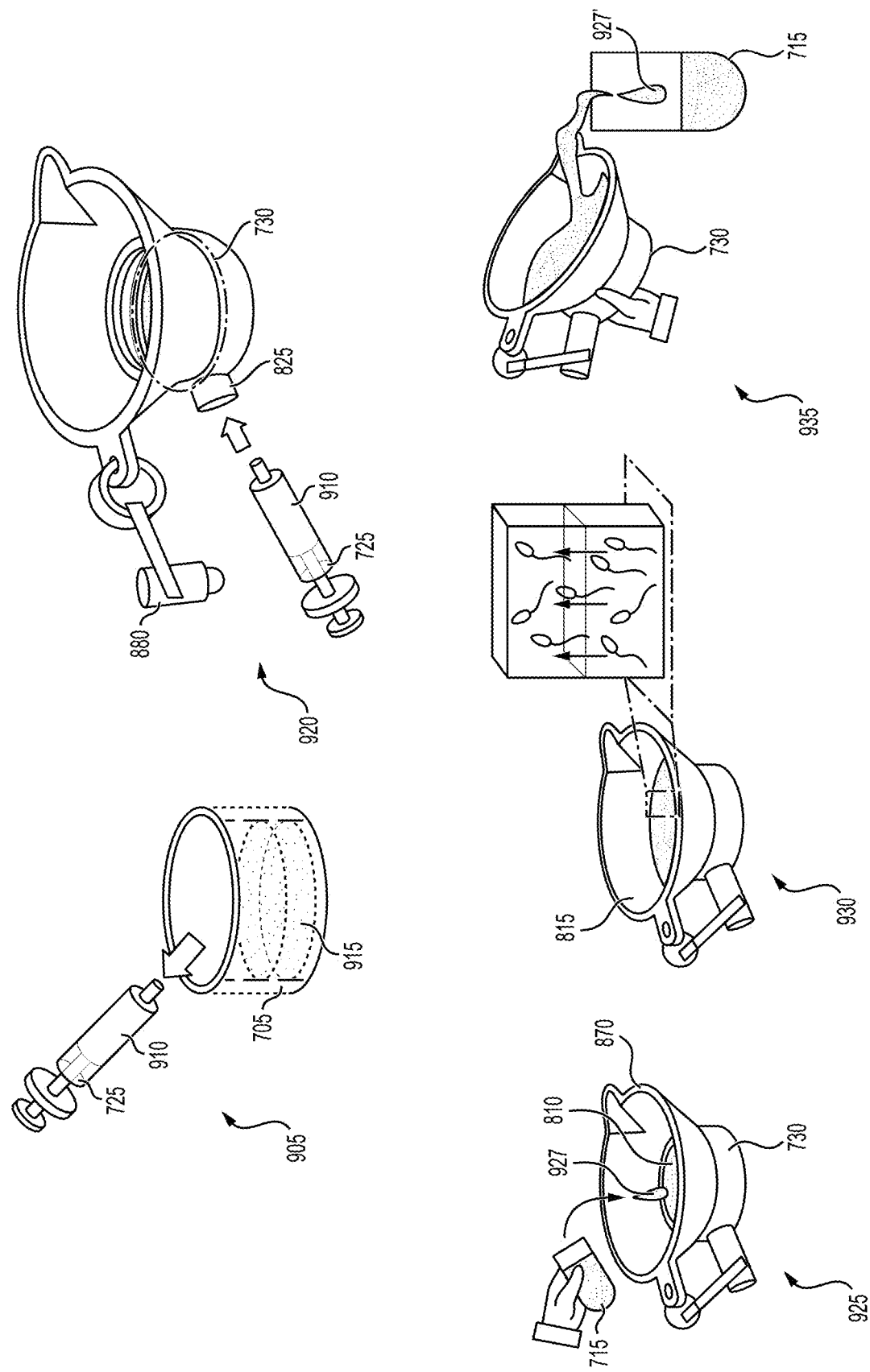
FIG. 9 depicts a flow diagram of an exemplary process for operation of the sample collection kit of FIG. 7.

FIG. 9 illustrates an operational flow 900 for using the analysis system 730. At step 905, the loading device 725 is operated to load an aliquot 910 (e.g., about 1 mL) of a male fertility sample 915 from the first container 705, which may then be sealed, e.g., using the first cap 710 (not show). At step 920, the aliquot 910 is loaded via the inlet 825 into the chamber 820 (not shown, see FIG. 8) of the analysis system 730, and the inlet cap 880 is operated to seal the inlet 825.

At step 925, media 927 (e.g., about 10 mL) is transferred from the second container 715 to the analysis system 730 via the opening 897, e.g., until the media 927 in the analysis system 730 saturates a side of the porous membrane 810 facing toward the second portion 815. The porous membrane 810, once saturated, is configured to act as a migration pathway for motile sperm in the aliquot to travel into the media in the second portion 815.

At step 930, the analysis system 730 is kept at room temperature for about one hour. During this period of time, motile sperm from the aliquot 910 migrate through pores of the porous membrane 810 and into the media 927 residing within the second portion 815 of the analysis system 730. The motile sperm that progress through the pores of the porous membrane 810 migrate against gravity and isolate from dead, unviable, or immotile in the first portion 805. Normal sperm have a spherical head shape that is around 10 um² in area. Micropores of the porous membrane 810 having a diameter that is within a general range of the sperm head size allow for only sperm that are motile to pass through the micropores. Dead, unviable, or immotile sperm are unable to progress to or through the micropores due to their lack of swimming ability or normal sperm head morphology/size. Instead, such non-motile sperm are affected by gravity and remain in the first portion 805. At step 935, the analysis system 730 is operated to remove the media 927', which includes a motile portion of the aliquot 910 that migrated as discussed above, from the analysis system 730 and into the second container 715. For example, a user may tip the analysis system 730 in order to pour out the media 927' from the second portion 815 and into the second container 715. In some embodiments, such operation provides for ergonomic interaction and ease-of-use. For example, a user need only manipulate the analysis system 730 from easily graspable surfaces that are never in contact with either the media or the sample.

Thereafter, the second container 715 may be sealed, e.g., using the cap 720, and the analysis system 730 may be disposed of. The first container 705 and second container 7145 may then be loaded into the transport case 735 for transport to the testing facility 140, e.g., via the courier 120 (not shown).

In some embodiments, an analysis system 730 as discussed in one or more of the embodiments above may reduce an amount of media needed to conduct (e.g., fertility) analysis. For instance, only a fill portion of the second portion 815 needs to be filled, rather than an entire basket as in other embodiments. In an example, submerging a basket may utilize about 10 mL or more of media, while only about 2 mL of media may be needed to fill the analysis system 730 up to the fill line defined by the lip 875. In another example, the analysis system 730 may facilitate an improved interface between the aliquot and the media. For instance, in some cases, a patient may not properly submerge the basket in media, whereas any media introduced into the analysis system 730 is directed toward the porous membrane 810 and the chamber 820.

Figure 10:
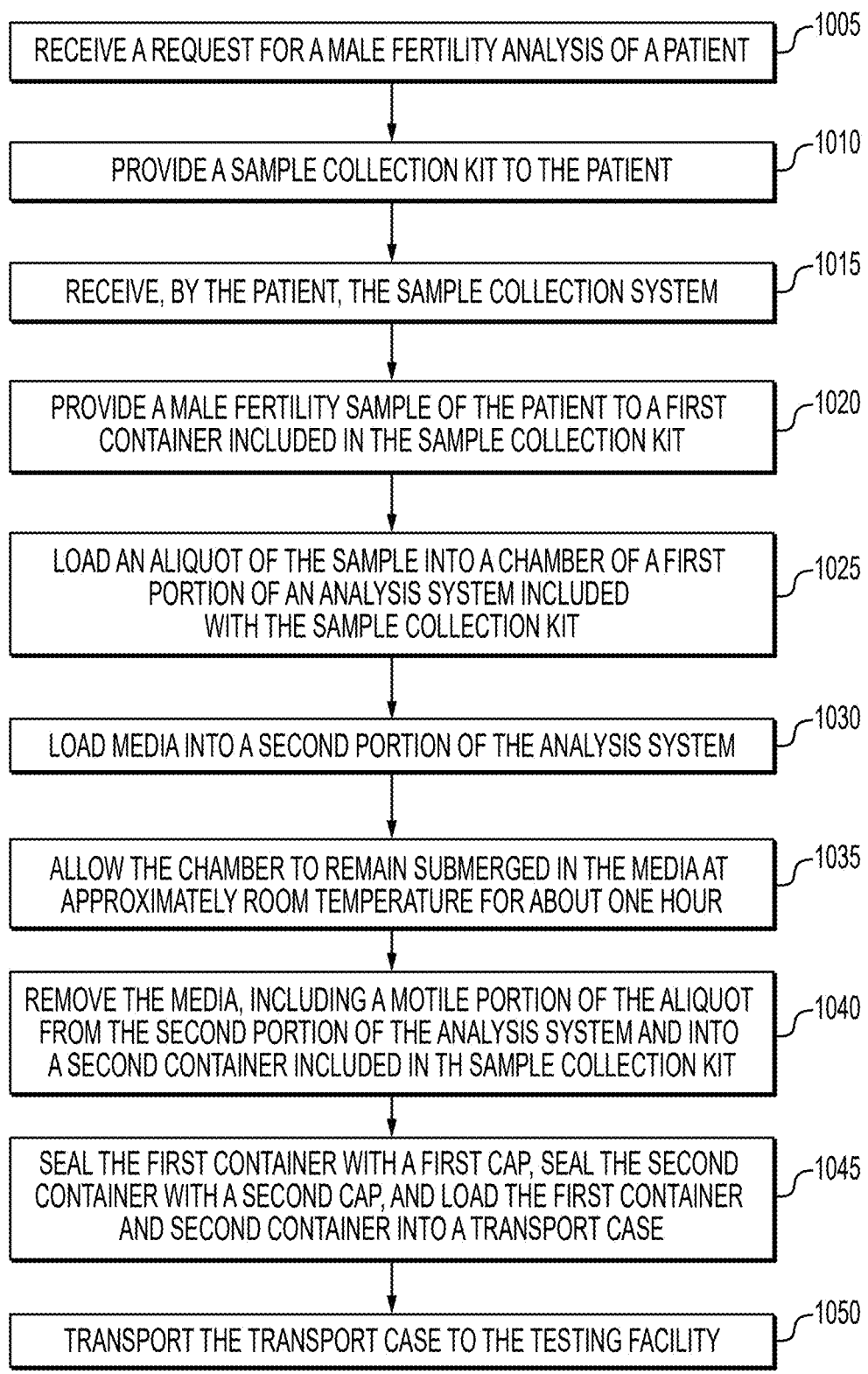
FIG. 10 depicts a flow diagram of an exemplary embodiment of using a sample collection kit, according to one or more embodiments.

FIG. 10 is a flow diagram illustrating an exemplary embodiment of a method for collecting a male fertility sample via a sample collection system 125. At step 1005, a facility device 115 of a testing facility 140 may receive a request for a male fertility analysis of a patient 130. In various embodiments, the request is received from a provider 135 via a provider device 110, from the patient 130 via a user device 105, etc. At step 1010, the testing facility 140 may provide a sample collection kit 700 to the patient 130. In various embodiments, sample collection kit 700 may be provided via the provider 135 (e.g., during a patient visit), via the courier 120 (e.g., as a delivery to a location 145 associated with the patient 130 such as their home address), or the like. In some embodiments, the testing facility may generate a unique identifier associating the sample collection kit 700 with the patient 130 and/or the provider 135, and may include or affix a label or other indication of the unique identifier with the sample collection kit 700. In some embodiments, the testing facility 140 may register the sample collection kit 700 with a medical data system associated with the provider 135, or the like.

At step 1015, the patient 130 may receive the sample collection kit 700. At step 1020, the patient 130 may provide a male fertility sample to a first container 705 included in the sample collection kit 700. At step 1025, the patient 130 may load an aliquot of the sample into a chamber 820 of an analysis system 730 included with the sample collection kit 700, e.g., via a loading device 725 and into an inlet 825 in a first portion 805 of the analysis system 730.

At step 1030, the patient 130 may load media from a second container 715 into the analysis system 730, e.g., via an opening 897 in a second portion 815 of the analysis system 730 until the media has saturated the porous membrane 810, and/or until the media reaches a lip 875 acting as a fill line. As a result, the porous membrane 810 may form an interface between the aliquot and the media. At step 1035, the analysis system 730 may be kept at about room temperature for about an hour, during which a motile portion of sperm in the aliquot may migrate through the porous membrane 810 and into the second portion 815 of the analysis system 730.

At step 1040, the patient 130 may operate the analysis system 730 to remove the media, along with a motile portion of the aliquot, from the analysis system 730 and into the second container 715. For instance, the patient 130 may leverage the cup-like shape of the analysis system 730 to pour the media and motile portion into the second container 715. At step 1045, the patient 130 may seal the first container 705 and the second container 715 with caps 710 and 720, respectively, and may load the first container 705 and second container 715 into a transport case 735. At step 1050, the patient 130 may cause the transport case 735 to be transported to a testing facility 140, e.g., via a courier 120. Thereafter, the testing facility 140 may analyze a male fertility of the patient 130, e.g., via one or more techniques discussed above.

In a conventional process, in order to account for the approximately one hour time constraint discussed above to consider a viable sample, rapid drop-off of the sample to a testing facility if produced at home, or on-site production of the sample is required. However, there are challenges regarding the requirements of the conventional analysis procedure. Semen analysis labs are specialized labs with limited locations, and thereby are not widely accessible to patients. Patients, particularly those in remote locations, are required to travel long distances to an analysis lab, adding both time and cost burdens. In the case of on-site production, the labs have limited capacity and thus patients can incur lengthy queuing periods. The public conditions of on-site production could also result in privacy and comfort issues. In the case of sample drop-off, the one hour time requirement is burdensome and constraining, and patients are often not readily available for drop-off. These challenges collectively hinder the widespread occurrence of semen analysis and highlight the need for a semen analysis process that is more accessible and available. To perform a comparative analysis between the subject matter of this disclosure and a conventional analysis process, the following experiments were conducted.

EXPERIMENTAL RESULTS

Experiment 1—Viability of Three-Dimensional Printed Components

Three-dimensional printing generally includes deposition of material in layers. To validate whether this layered structure has an impact on sperm motility analysis, the following experiment was conducted.

A three-dimensional printer was used to fabricate a container of comparable size to a standard culture tube (control). Five biocompatibility tests were performed, and revealed that there were no significant differences in the sperm vitality and motility between the control and 3D printed containers at each time point over a 1.5 hour testing duration. For each test, 1 ml of semen were introduced into the 3D printed and control containers, and were analyzed at regular half-hour intervals. Semen analysis was performed using a Sperm Class Analyzer (SCA) Computer Assisted Semen Analysis (CASA) system. FIGS. 11A-D illustrate the results of these biocompatibility tests.

FIG. 11A depicts a graph of a distribution from the tests of percentage viability of sperm incubated in the control and 3D printed containers at time zero and at 1.5 hours, and FIG. 11B depicts a graph of an average across the viability tests at time zero and at 1.5 hours. As can be seen in FIGS. 11A and 11B, there is no significant change in viability between the control (white bars) and the 3D printed container (hatched bars).

FIG. 11C depicts graph of a distribution from the tests of percentage motility of sperm incubated in the control and 3D printed containers at half-hour time increments, and FIG. 11D depicts a graph of an average across the motility tests at half-hour time increments. As can be seen in FIGS. 11C and 11D, there is no significant change in detected motility between the control (white bars) and the 3D printed container (hatched bars).

Experiment 2—Performance of Analysis Platform

Performance of the analysis platform 330 as discussed above with regard to FIG. 3 was examined across several parameters, including the retrieved sperm concentration, the sperm retrieval rate, and the percentage of motile sperm at various processing times (e.g., at 0.5, 1, and 1.5 hours). For this experiment, the analysis platform 330 was fabricated using a 3D printer. The bottom chamber 375 was designed to support up to 1 mL of semen (22 mm diameter, 3 mm depth) and the dedicated inlet 350 (4 mm diameter) allowed for the insertion of a standard 1 mL loading syringe 225. The porous membrane 365 was a nylon mesh membrane with 10 µm diameter pores. A cutting plotter was used to cut the membrane, and double-sided adhesive tapes into the desired circular shapes (25 mm diameter). The cut double-sided adhesive tapes were adhered to both the front and back of the membrane 365. The platform 330 was assembled by adhering the membrane 365 on the first portion 360 and applying the second portion 370 onto the membrane 365 overlaid the first portion 360. The membrane 365 was adhered to both the first portion 360 and the second portion 370.

Twenty-three patient semen samples were obtained from a testing facility. The samples were fresh and used for testing after the standard semen analysis, within 1 hour of patient drop-off or on-site collection. The samples were considered leftover bio-waste post standard semen analysis. Patients provided informed consent for research purposes.

An assay for each of the twenty-three samples consisted of several steps. The platform 330 was first loaded with 1 mL of semen. A syringe 225 was used to acquire 1 mL of semen from the collection container 200. The syringe 225 was inserted into the inlet 350 of the platform 330 and the semen aliquot was introduced into the chamber 375. The inlet 350 was closed via the cap 232. A container 210 (40 mL capacity) was filled with PureSperm™ wash medium (10 mL). The platform 330 with semen loaded was placed in the media-filled container 210 with the bottom chamber 375 fully submerged within the media and the membrane 365 fully covered by the media. The platform 330 was left submerged in the container 210 for 1 hour at room temperature. During the incubation period, motile sperm were separated as they migrated from the platform 330, through the pores, to the media. After 1 hour, the platform 330 was removed from the container 210 and disposed of. The motile sperm within the media were used for semen analysis. As noted above, samples were tested at various processing times (e.g., at 0.5, 1, and 1.5 hours).

Semen analysis was performed using SCA with a CASA system. The sample retrieved from the platform 330 and the original sample were assessed for sperm motility and total concentration. The SCA system computes the sperm motility (percentage and concentration) and total concentration based on a series of videos captured under a microscope. For the video captures, a Leja chamber microscope slide was prepared for each. An aliquot (5 µL) of the sample retrieved from the platform and a similar aliquot from the original sample were each loaded in the chamber of their respective Leja slide. Each slide was assessed under the microscope at 10× magnification. The SCA system was used to capture videos from 12 fields within the slide. The videos of the sperm were analyzed by the SCA system to generate an approximation of the percentage and concentration of the motile sperm, along with the total concentration of the sample.

Figure 12A:
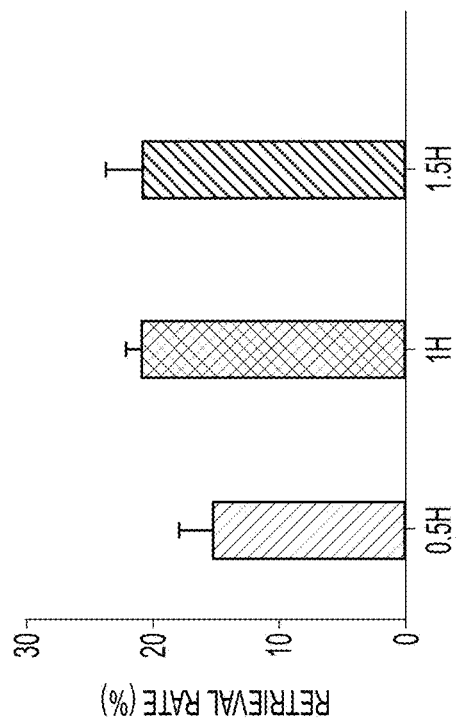
FIGS. 12A-E depict graphs of experimental results from an experimental assay of sperm concentration in multiple samples to compare concentration in the raw samples against concentration over time from incubation using the sample collection system of FIG. 2.
Figure 12B:
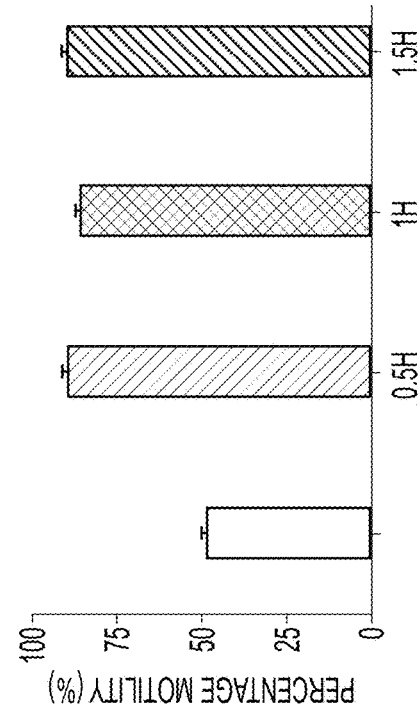
Figure 12C:
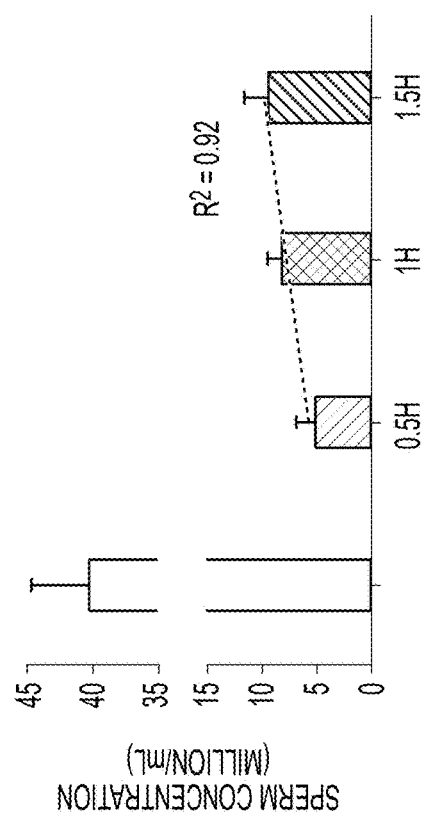
Figure 12D:
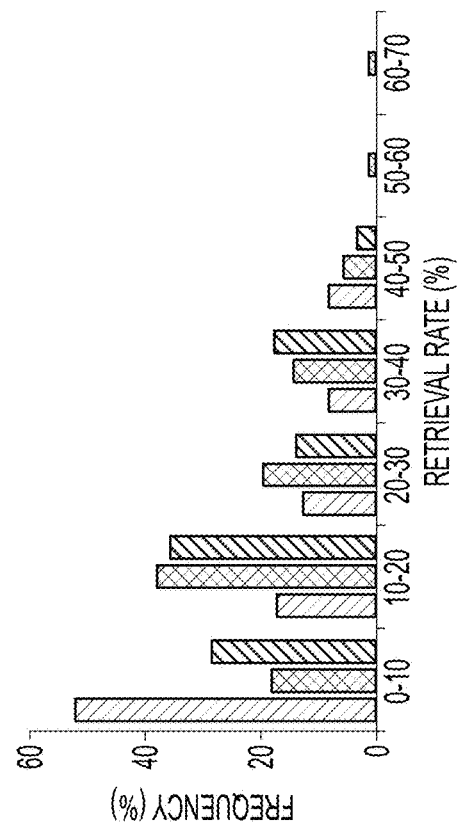
Figure 12E:
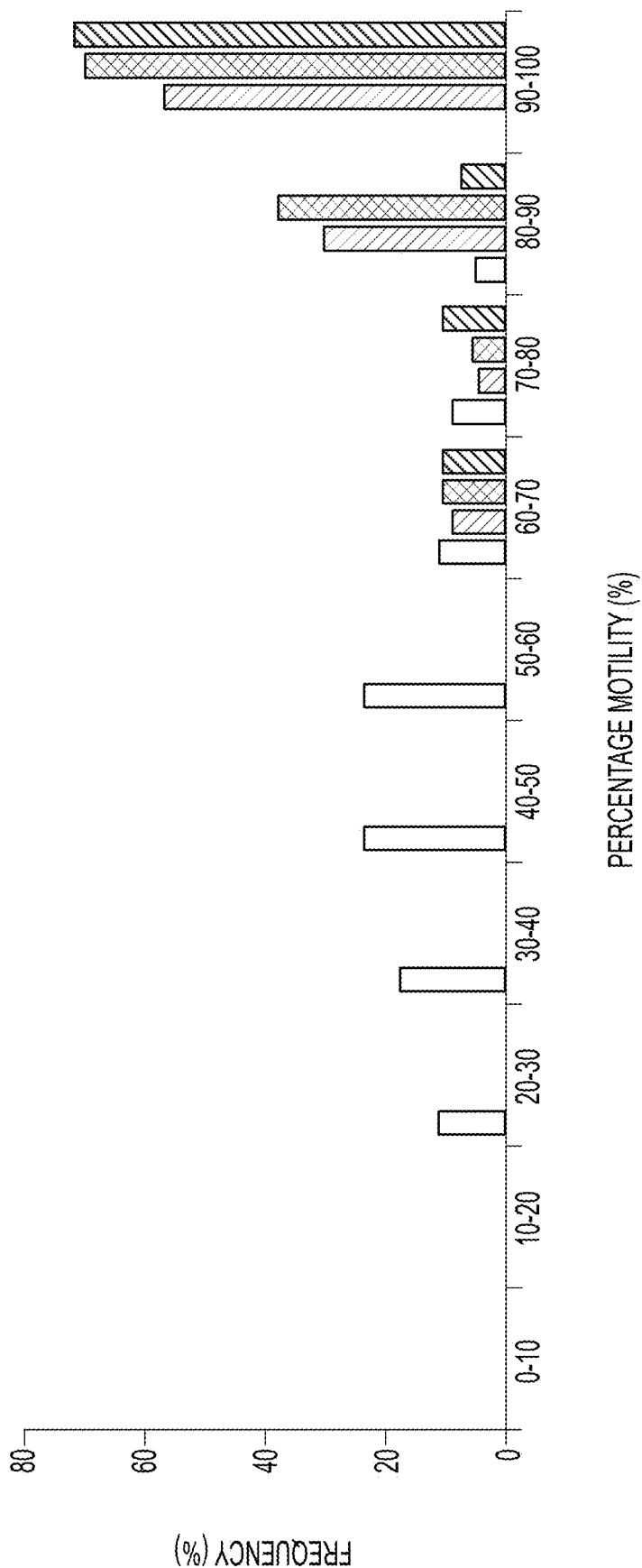

FIGS. 12A-E illustrate the results of the assay above. Given an average concentration of 40 million sperm/mL in the original sample (white bar), the platform 330 retrieved over 5.1, 8.4, and 9.4 million sperm/mL in 0.5, 1, and 1.5 hours, respectively (thin hatched, cross-hatched, and thick hatched bars, respectively). The retrieved sperm concentration demonstrated a linear increase (R2=0.92) with time. See, e.g., FIG. 12A. The linearity of the relationship between processing time and sperm concentration suggests that the platform 330 can effectively retrieve sperm at a rate proportional to time, offering predictable and scalable performance. The ability to predict the sperm concentration offers several key advantages. It allows for a sample to be initially collected without same-day analysis, and for the analysis to be performed later without the need for live sperm to determine the sperm concentration. The scalability of the platform 330 enables the processing time to be readily adjusted to generate the concentration that would be the most suitable for analysis. Based on the concentration outcomes, the sperm retrieval rate (the percentage of sperm retrieved from the original sample) was computed, in which the platform 330 retrieved over 15.2%, 20.6%, and 20.8% in 0.5, 1, and 1.5 hours, respectively. See e.g., FIG. 12B. FIG. 12C illustrates a distribution of retrieval rates amongst the twenty-three assays for the platform at 0.5, 1, and 1.5 hour testing times. FIG. 12D illustrates an average percentage of motile sperm of raw and the retrieved cohort from the platform 330 at 0.5, 1, and 1.5 hour testing times, and FIG. 12E illustrates a distribution of the same.

The distribution illustrated in FIG. 12E was examined. The control had a broader distribution, indicating a wide range of motile sperm percentages, which was expected given the heterogeneous nature of unprocessed semen. In contrast, the platform-330-processed populations exhibited a much narrower distribution of motility, regardless of processing time. At 0.5 hours, the distribution showed a tighter localization around higher motility percentages, indicating that the platform 330 was effective at selectively retrieving motile sperm even after a short processing time. As the processing time increased to 1 hour and 1.5 hours, the distribution remained narrow, with the peak motility percentages shifting slightly higher. The results suggest that while the motility improvement was minimal beyond 0.5 hours, the platform 330 provided a consistent and predictable retrieval of motile sperm across all time points. The platform 330 thus provides a scalable, predictable, and reliable approach in retrieving motile sperm from semen, demonstrating consistent and optimal performance with respect to the retrieved sperm concentration, retrieval rate, and sperm motility.

Figure 13A:
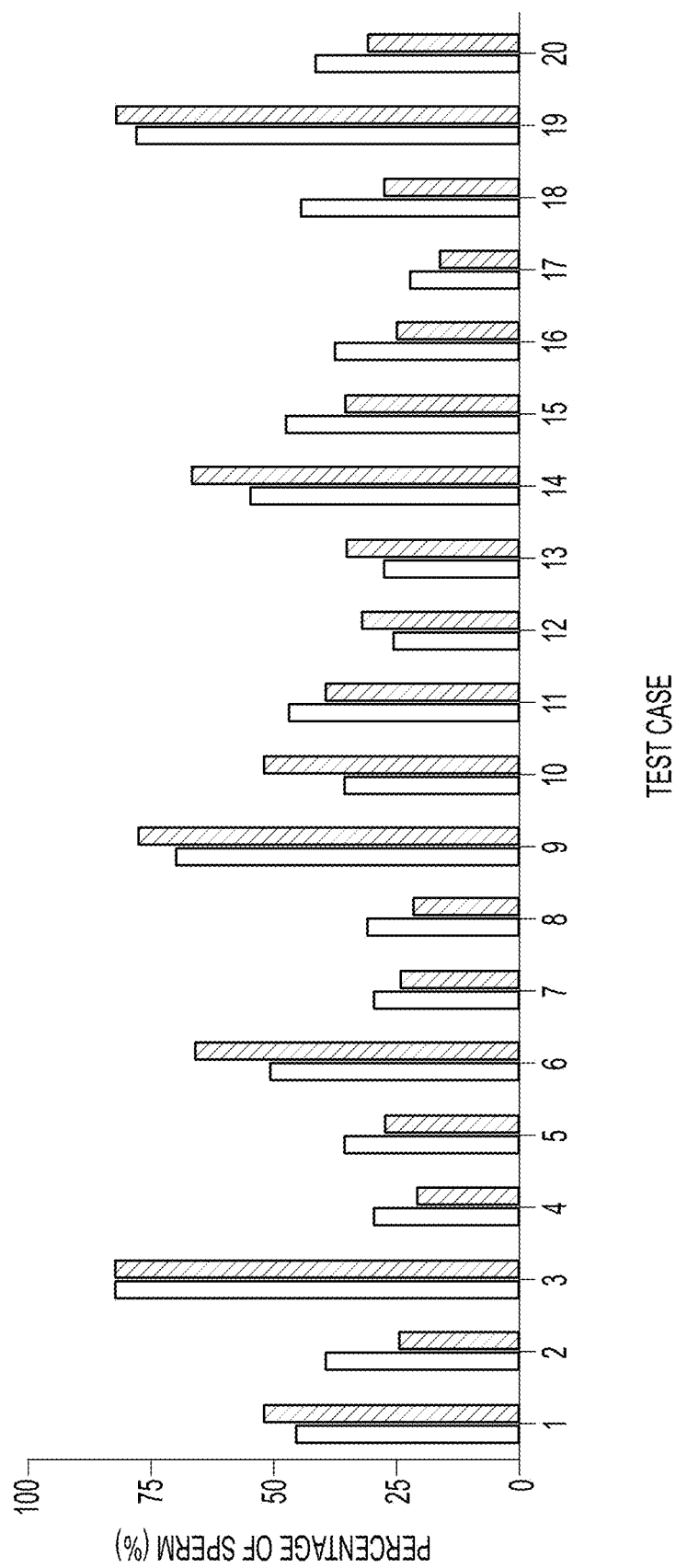

FIGS. 13A-D depict a direct comparison between results from the platform 330 and standard semen analysis. FIG. 13A compares the percentage of motile sperm retrieved across twenty test cases for the platform 330 against standard analysis, and FIG. 13B illustrates the distribution of those results. For the majority of the tests, both the platform-330-based estimate and SCA followed similar trends in motile sperm percentage. The results suggest that the platform 330 estimates closely aligned with those of the SCA—and the existing clinically expected outcomes—across a range of samples. In the distribution illustrated in FIG. 13b, the interquartile range (IQR) was similar for the two methods, indicating that both the platform 330 estimate and SCA consistently produced comparable percentages of motile sperm. The overlap in IQR demonstrates that, in terms of central tendency, both methods yielded motile sperm outcomes with similar variability. The whiskers showed minimal difference between the platform 330 estimate and SCA. This similarity in distribution spread indicates that the two methods handle the extremes of sample variability (either low or high motile sperm counts) in a comparable manner—neither method produces significantly more outliers than the other, reinforcing that both approaches maintain stable and predictable performance even in more variable sample conditions. The median values were centered within a similar range for both methods, highlighting that the typical outcome for either method would be consistent. The similarities in the distribution of motile sperm percentages between the platform 330 estimate and SCA indicate that the platform 330 estimate is comparable to that of the conventional SCA in terms of variability, range, and typical outcomes. FIG. 13C illustrates the relationship between results from the platform 330 against the standard results, indicated by a trend line with an r-squared value of 0.79. A strong linear correlation was observed between the outcomes of platform 330 and SCA, indicating that the motile sperm percentages produced by the platform 330 were highly comparable to those produced by SCA. The linearity highlights the high degree of correlation between the two methods, suggesting that both platform 330 and SCA respond similarly to variations in the motile sperm content of raw semen samples. FIG. 13D compares the average for motile percentage retrieved between the platform 330 and standard analysis. On average, the motile sperm percentages produced by the platform 330 estimate and SCA were 42% and 44%, respectively. The minor difference in average motility between the two methods was not statistically significant, suggesting that the platform 330 estimate performs on par with the conventional SCA in determining motile sperm percentage.

In general, any process or operation discussed in this disclosure that is understood to be computer-implementable, such as the processes illustrated in FIGS. 5, 6, 9, and 10 may be performed by one or more processors of a computer system, such any of the computer systems or devices in the environment 100 of FIG. 1, as described above. A process or process step performed by one or more processors may also be referred to as an operation. The one or more processors may be configured to perform such processes by having access to instructions (e.g., software or computer-readable code) that, when executed by the one or more processors, cause the one or more processors to perform the processes. The instructions may be stored in a memory of the computer system. A processor may be a central processing unit (CPU), a graphics processing unit (GPU), or any suitable types of processing unit.

A computer system, such as a system or device implementing a process or operation in the examples above, may include one or more computing devices, such as one or more of the computer systems or devices in FIG. 1. One or more processors of a computer system may be included in a single computing device or distributed among a plurality of computing devices. A memory of the computer system may include the respective memory of each computing device of the plurality of computing devices.

Figure 14:
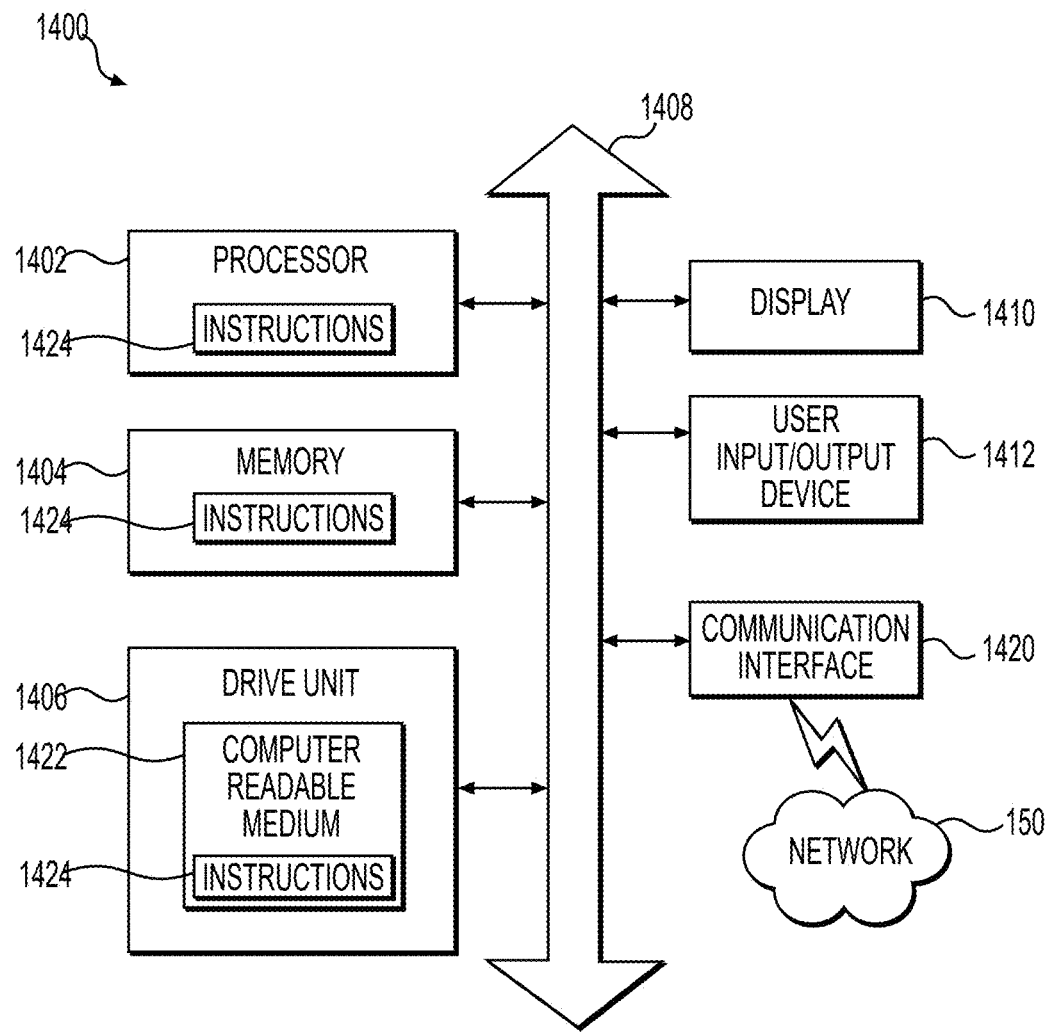
FIG. 14 depicts a block diagram of an exemplary computer system.

FIG. 14 is a simplified functional block diagram of a computer 1400 that may be configured as a device for executing the methods of FIGS. 2 and 3, according to exemplary embodiments of the present disclosure. For example, the computer 1400 may be configured as the facility device 115 and/or another computer system according to exemplary embodiments of this disclosure. In various embodiments, any of the computer systems herein may be a computer 1400 including, for example, a data communication interface 1420 for packet data communication. The computer 1400 also may include a central processing unit ("CPU") 1102, in the form of one or more processors, for executing program instructions. The computer 1400 may include an internal communication bus 1108, and a storage unit 1406 (such as ROM, HDD, SDD, etc.) that may store data on a computer readable medium 1422, although the computer 1400 may receive programming and data via network communications. The computer 1400 may also have a memory 1404 (such as RAM) storing instructions 1424 for executing techniques presented herein, although the instructions 1424 may be stored temporarily or permanently within other modules of computer 1400 (e.g., processor 1402 and/or computer readable medium 1422). The computer 1400 also may include input and output ports 1412 and/or a display 1410 to connect with input and output devices such as keyboards, mice, touchscreens, monitors, displays, etc. The various system functions may be implemented in a distributed fashion on a number of similar platforms, to distribute the processing load. Alternatively, the systems may be implemented by appropriate programming of one computer hardware platform.

Program aspects of the technology may be thought of as "products" or "articles of manufacture" typically in the form of executable code and/or associated data that is carried on or embodied in a type of machine-readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of the mobile communication network into the computer platform of a server and/or from a server to the mobile device. Thus, another type of media that may bear the software elements includes optical, electrical and electromagnetic waves, such as used across physical interfaces between local devices, through wired and optical landline networks and over various airlinks. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

It should be appreciated that in the above description of exemplary embodiments of the invention, various features of the invention are sometimes grouped together in a single embodiment, figure, or description thereof for the purpose of streamlining the disclosure and aiding in the understanding of one or more of the various inventive aspects.

Furthermore, while some embodiments described herein include some but not other features included in other embodiments, combinations of features of different embodiments are meant to be within the scope of the invention, and form different embodiments, as would be understood by those skilled in the art.

Thus, while certain embodiments have been described, those skilled in the art will recognize that other and further modifications may be made thereto without departing from the spirit of the invention, and it is intended to claim all such changes and modifications as falling within the scope of the invention. For example, functionality may be added or deleted from the block diagrams and operations may be interchanged among functional blocks. Steps may be added or deleted to methods described within the scope of the present invention.

The above disclosed subject matter is to be considered illustrative, and not restrictive, and the appended claims are intended to cover all such modifications, enhancements, and other implementations, which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description. While various implementations of the disclosure have been described, it will be apparent to those of ordinary skill in the art that many more implementations and implementations are possible within the scope of the disclosure.

I claim:

1. A system for male fertility analysis, comprising:
a first portion, including:
   a chamber with an opening and a concave bottom opposite the opening; and
   an inlet into the chamber;
a second portion; and
a porous membrane extending over the opening of the chamber and secured between the first portion and the second portion, such that the porous membrane is configured to act as a migration path for a motile portion of an aliquot of a male fertility sample loaded into the chamber via the inlet to move into media loaded into the second portion,
wherein the second portion is operable to pour the media and the motile portion of the aliquot of the male fertility sample out from the system; and
wherein the second portion includes a lip configured to receive an outer rim of the first portion, such that the porous membrane is secured therebetween.

2. The system of claim 1, wherein the inlet is oriented toward the chamber such that an axis of the inlet does not intersect with the porous membrane.

3. The system of claim 1, further comprising:
a cap that is configured to seal the inlet.

4. The system of claim 3, wherein the cap is movably connected to the second portion.

5. The system of claim 1, wherein the second portion includes:
a first opening configured to receive the media;
a second opening that is in communication with the first opening and with the porous membrane, the first portion having a first diameter that is larger than a second diameter of the second portion; and
a wall that tapers from the first diameter at the first opening to the second diameter at the second opening.

6. The system of claim 1, wherein:
the inlet includes a neck portion extending from the first portion; and
the second portion includes a collar portion configured to fit around the neck portion.

7. The system of claim 1, wherein the porous membrane is a membrane with 10 μm diameter pores.

8. The system of claim 1, wherein the first and second portions have been formed, via three-dimensional printing, from a plurality of connected layers of material.

9. The system of claim 1, wherein the second portion further includes a fill indicator that identifies a fill level for the media to submerge the porous membrane.

10. The system of claim 9, wherein the fill indicator is formed by a lip disposed between the first opening and the second opening.

11. The system of claim 1, wherein the second portion further includes a spout configured to facilitate the pouring out of the media and the motile portion of the aliquot of male fertility sample.

12. The system of claim 1, further comprising:
a supply of the media;
a first container configured to receive the media and the motile portion of the aliquot of male fertility sample poured out from the system; and
a second container configured to receive a portion of the male fertility sample remaining from or acting as a source of the aliquot.

13. A system for male fertility analysis, comprising:
a first portion, including:
a chamber with an opening and a concave bottom opposite the opening; and
an inlet into the chamber;
a second portion;
a porous membrane extending over the opening of the chamber and secured between the first portion and the second portion, such that the porous membrane is configured to act as a migration path for a motile portion of an aliquot of a male fertility sample loaded into the chamber via the inlet to move into media loaded into the second portion; and
a cap that is configured to seal the inlet,
wherein the second portion is operable to pour the media and the motile portion of the aliquot of the male fertility sample out from the system, and
wherein the cap is movably connected to the second portion.

14. The system of claim 13, wherein the inlet is oriented toward the chamber such that an axis of the inlet does not intersect with the porous membrane.

15. The system of claim 13, wherein the porous membrane is a membrane with 10 μm diameter pores.

16. The system of claim 13, wherein, wherein the second portion further includes a fill indicator that identifies a fill level for the media to submerge the porous membrane.

17. The system of claim 16, wherein the fill indicator is formed by a lip disposed between the first opening and the second opening.

18. The system of claim 13, wherein the second portion further includes a spout configured to facilitate the pouring out of the media and the motile portion of the aliquot of male fertility sample.

19. A system for male fertility analysis, comprising:
a first portion, including:
a chamber with an opening and a concave bottom opposite the opening; and
an inlet into the chamber;
a second portion; and
a porous membrane extending over the opening of the chamber and secured between the first portion and the second portion, such that the porous membrane is configured to act as a migration path for a motile portion of an aliquot of a male fertility sample loaded into the chamber via the inlet to move into media loaded into the second portion,
wherein the second portion is operable to pour the media and the motile portion of the aliquot of the male fertility sample out from the system; and
wherein the second portion includes:
a first opening configured to receive the media;
a second opening that is in communication with the first opening and with the porous membrane, the first portion having a first diameter that is larger than a second diameter of the second portion; and
a wall that tapers from the first diameter at the first opening to the second diameter at the second opening.

20. The system of claim 19, wherein the second portion further includes a spout configured to facilitate the pouring out of the media and the motile portion of the aliquot of male fertility sample.

* * * * *